(12) United States Patent
Ahsan

(10) Patent No.: US 12,157,120 B2
(45) Date of Patent: Dec. 3, 2024

(54) EMULATING DISEASE IN A MICROFLUIDIC SYSTEM WITH A RELEASABLE INTERFACIAL FILM AND COMMUNICATION BETWEEN NON-GEL AQUEOUS SOLUTIONS

(71) Applicant: CALIFORNIA NORTHSTATE COLLEGE OF PHARMACY, LLC, Elk Grove, CA (US)

(72) Inventor: Fakhrul Ahsan, Elk Grove, CA (US)

(73) Assignee: CALIFORNIA NORTHSTATE COLLEGE OF PHARMACY, LLC, Elk Grove, CA (US)

( * ) Notice: Subject to any disclaimer, the term of this patent is extended or adjusted under 35 U.S.C. 154(b) by 0 days.

(21) Appl. No.: 18/406,610

(22) Filed: Jan. 8, 2024

(65) Prior Publication Data

US 2024/0181447 A1 Jun. 6, 2024

Related U.S. Application Data

(62) Division of application No. 17/865,021, filed on Jul. 14, 2022, now Pat. No. 11,944,969.

(Continued)

(51) Int. Cl.
*B01L 3/00* (2006.01)
*C12M 3/00* (2006.01)

(52) U.S. Cl.
CPC ....... *B01L 3/502715* (2013.01); *C12M 21/08* (2013.01); *B01L 2300/0867* (2013.01)

(58) Field of Classification Search
CPC ...... B01L 3/502715; B01L 2300/0867; C12M 21/08
See application file for complete search history.

(56) References Cited

U.S. PATENT DOCUMENTS 9,261,496 B2   2/2016  Kamm et al.
10,767,149 B2   9/2020  Kamm et al.
(Continued)

FOREIGN PATENT DOCUMENTS

WO   WO 2020/081288   4/2020
WO   PCT/US2022/037173   7/2022

OTHER PUBLICATIONS

U.S. Appl. No. 18/588,830, filed Jul. 28, 2021, Ahsan.
(Continued)

*Primary Examiner* — Brian J. Sines
(74) *Attorney, Agent, or Firm* — Brian S. Boyer; SYNDICATED LAW, PC

(57) ABSTRACT

Methods are provided for emulating disease in a microfluidic system with a releasable interfacial film component that allows communication between non-gel aqueous solutions to emulate natural physiological conditions. The systems and methods emulate cellular communication in a disease state in a more accurate aqueous environment and provide data on the interaction between the cells that can be used to develop a treatment for a subject in need. The systems and methods also can be used to assess the effect of a particular treatment, such as a drug therapy, radiation therapy, or a combination thereof, for example. The systems and methods can show how a particular therapy is affected by any of several known factors including, but not limited to, the sex of the subject, the age of the subject, hereditary factors or other genetic predispositions, as well as perhaps other physiological states of the subject, or a combination thereof.

12 Claims, 5 Drawing Sheets

Related U.S. Application Data

(60) Provisional application No. 63/226,733, filed on Jul. 28, 2021.

(56) References Cited

U.S. PATENT DOCUMENTS

| | | | |
|---|---|---|---|
| 11,944,969 B2* | 4/2024 | Ahsan | B01L 3/502753 |
| 2019/0017999 A1 | 1/2019 | Jeon et al. | |
| 2023/0035822 A1 | 2/2023 | Ahsan | |

OTHER PUBLICATIONS

U.S. Appl. No. 63/266,733, filed Jul. 28, 2021, Ahsan.

Written opinion and search report for PCT/U82022/037173, Jul. 14, 2022, California Northstate College of Pharmacy, LLC.

Al-Hilal, T., et al. Multi-channel chips to simulate pulmonary arterial hypertension (PAH) pathophysiology and screen anti-PAH drugs. In 21st International Conference on Miniaturized Systems for Chemistry and Life Sciences, MicroTAS 2017 p. 1068-1069.

Al-Hilal, T., et al. Pulmonary-arterial-hypertension (PAH)-on-a-chip: fabrication, validation and application. The Royal Society of Chemistry. (2020) DOI: 10.1039/d0lc00605j.

Asmani. M., et al. Fibrotic microtissue array to predict anti-fibrosis drug efficacy. Nature Communications. 9(2066): 1-12 (2018). DOI: 10.1038/s41467-018-04336-z.

Baeyens, N., et al. Endothelial fluid shear stress sensing in vascular health and disease. J Clin Invest. 126(3):821-828 (2016) DOI: 10.1172/JCI83083.

Bhatia. S.N., et al. Microfluidic organs-on-chips. Nature Biotechnology. p. 1-13 (2014) DOI: 10.1038/nbt.2989.

Bonnet, S., et al. Shear Stress Maladaptation in Pulmonary Arterial Hypertension. American Journal of Respiratory and Critical Care Medicine. 193(12):1331-1332 (2016).

Bonnet, S., et al. Translating Research into Improved Patient Care in Pulmonary Arterial Hypertension. Am J Respir Crit Care Med. 195(5):583-595 (2017) Originally published as DOI: 10.1164/rccm. 201607-1515PP on Sep. 20, 2016.

Budas, G.R., et al. ASK1 inhibition halts disease progression in preclinical models of pulmonary arterial hypertension. American Thoracic Society. p. 1-61 (2017) DOI: 10.1164/rccm.201703-05020C.

Bummer. P.M., et al. Surfactant disposition in rats with monocrotaline-induced pneumotoxicity. Toxicology. 90: 53-62 (1994).

Campisi, M., et al. 3D self-organized microvascular model of the human blood-brain barrier with endothelial cells, pericytes and astrocytes. Biomaterials 180:117-129 (2018).

Cho, M., et al. Modular 3D In Vitro Artery-Mimicking Multichannel System for Recapitulating Vascular Stenosis and Inflammation. Micromachines 12(12) (2021).

Chung, S., et al. Cell migration into scaffolds under co-culture conditions in a microfluidic platform. Lab on a Chip. 9(2): 269-275 (2009).

Colvin, K.L., et al. Animal Models of Pulmonary Hypertension: Matching Disease Mechanisms to Etiology of the Human Disease. J Pulm Respir Med. 4(4) (2015).

Comhair, S.A.A., et al. Human Primary Lung Endothelial Cells in Culture. Am J Respir Cell Mol Biol. 46(6):723-730 (2012) Originally Published in Press as DOI: 10.1165/rcmb.2011-0416TE on Mar. 15, 2012.

Dempsie, Y., et al. Development of pulmonary arterial hypertension in mice over-expressing S100A4/Mts1 is specific to females. Respiratory Research 12:159 (2011).

Ding. Y., et al. Biomimetic soft fibrous hydrogels for contractile and pharmacologically responsive smooth muscle. Acta Biomater. 74:121-130 (2018) DOI: 10.1016/j.actbio.2018.05.015.

Ezra Tsur, E., et al. Microfluidic Concentric Gradient Generator Design for High-Throughput Cell-Based Studies. Front Bioeng Biotechnol. 5(21) (2017).

Farahat, W.A., et al., Ensemble analysis of angiogenic growth in three-dimensional microfluidic cell cultures. PLoS One. 7(5): e37333 (2012).

Fernandez-Bonetti, P., et al. Peripheral Airways Obstruction in Idiopathic Pulmonary Artery Hypertension (Primary). Chest. 83(5): 732-738 (1983).

Firth, A.L, et al. Idiopathic pulmonary arterial hypertension. Dis Model Mech 3: 268-273 (2010) doi:10.1242/dmm.003616.

Gabler, N.B., et al. Race and Sex Differences in Response to Endothelin Receptor Antagonists for Pulmonary Arterial Hypertension. Chest. 141(1): 20-26 (2012).

Gao, Y., et al. Endothelial and Smooth Muscle Cell Interactions in the Pathobiology of Pulmonary Hypertension. Am J Respir Cell Mol Biol. 54(4):451-460 (2016) Originally Published in Press as DOI: 10.1165/rcmb.2015-0323TR on Jan. 8, 2016.

Greenway, S. S100A4/Mts1 Produces Murine Pulmonary Artery Changes Resembling Plexogenic Arteriopathy and Is Increased in Human Plexogenic Arteriopathy. American Journal of Pathology 164(1): 253-262 (2004).

Hajal, C., et al. The effects of luminal and trans-endothelial fluid flows on the extravasation and tissue invasion of tumor cells in a 3D in vitro microvascular platform. Biomaterials 265: 120470 (2021).

Hajal, C., et al. Engineered human blood-brain barrier microfluidic model for vascular permeability analyses. Nature Protocols. 17: 95-128 (2022).

Hopper, R.K., et al. In Pulmonary Arterial Hypertension, Reduced BMPR2 Promotes Endothelial-to-Mesenchymal Transition via HMGA1 and its Target Slug. Circulation. 133(18):1783-1794 (2016) DOI: 10.1161/CIRCULATIONAHA.115.020617.

Huang, C.P., et al. Engineering microscale cellular niches for three-dimensional multicellular co-cultures. Lap Chip. 9:1740-1748 (2009) DOI: 10.1039/b818401a.

Hye, T., et al. Newer insights into the pathobiological and pharmacological basis of the sex disparity in patients with pulmonary arterial hypertension. Am J Physiol Lung Cell Mol Physiol 320: L1025-L1037 (2021).

Hyung, S., et al. A 3D disease and regeneration model of peripheral nervous system-on-a-chip. Sci Adv. 7(5) (2021).

Ingber. D.E. Reverse Engineering Human Pathophysiology with Organs-on-Chips. Cell. 164:1105-1109 (2016) DOI: http://dx.doi.org/10.1016/j.cell.2016.02.049.

Jeon, J.S., et al. Human 3D vascularized organotypic microfluidic assays to study breast cancer cell extravasation. PNAS 112(1): 214-219 (2015).

Jönsson, A., et al. The FAST Pump, a low-cost, easy to fabricate, SLA-3D-printed peristaltic pump for multi-channel systems in any lab. HardwareX 8: e00115 (2020) https://doi.org/10.1016/j.ohx.2020. e00115.

Kamkaew. A., et al. Quantum Dot—NanoLuc Bioluminescence Resonance Energy Transfer Enables Tumor Imaging and Lymph Node Mapping In Vivo. J. Name. 00(1-3):1-5 (2013) Published as DOI: 10.1039/C6CC02764D on Apr. 28, 2016.

Keshavarz, A., et al. CAR, a Homing Peptide, Prolongs Pulmonary Preferential Vasodilation by Increasing Pulmonary Retention and Reducing Systemic Absorption of Liposomal Fasudil. Mol Pharm. 16(8):3414-3429 (2019) DOI: 10.1021/acs.molpharmaceut.9b0020.

Keshavarz, A., et al. Newer approaches and novel drugs for inhalational therapy for pulmonary arterial hypertension. Expert Opin Drug Deliv. 17(4): 439-461 (2020) DOI: 10.1080/17425247.2020. 1729119.

Kim, C., et al. A quantitative microfluidic angiogenesis screen for studying anti-angiogenic therapeutic drugs. Lap Chip. 15:301 (2015) DOI: 10.1039/c4lc00866a.

Kim, S., et al. Engineering of functional, perfusable 3D microvascular networks on a chip. Lap Chip. 13:1489 (2013).

Ko, J., et al. Human Ocular Angiogenesis-Inspired Vascular Models on an Injection-Molded Microfluidic Chip. Adv Healthc Mater. 8(15): e1900328 (2019).

Lee, P.J., et al. An Artificial Liver Sinusoid with a microfluidic endothelial-like Barrier for Primary Hepatocyte Culture. Biotechnology and Bioengineering 97(5): 1340-1346 (2007).

Low, L.A, et al. Tissue chips—innovative tools for drug development and disease modeling. Lab Chip 17: 3026-3036 (2017) doi:10.1039/c7lc00462a.

(56) References Cited

OTHER PUBLICATIONS

Lupinski, T., et al. An Arduino-based constant pressure fluid pump. Eur. Phys. J. E 44:14 (2021) https://doi.org/10.1140/epje/s10189-020-00002-9.

Lythgoe. M.P., et al. Why drugs fail in clinical trials in pulmonary arterial hypertension, and strategies to succeed in the future. Pharmacology and Therapeutics. (2016) DOI: http://dx.doi.org/10.1016/j.pharmthera.2016.04.012.

Mair, K.M., et al. Sex Affects Bone Morphogenetic Protein Type II Receptor Signaling in Pulmonary Artery Smooth Muscle Cells. Am J Respir Crit Care Med. 191(6):693-703 (2015) Originally Published in Press as DOI: 10.1164/rccm.201410-1802OC on Jan. 21, 2015.

Manbachi, A., et al. Microcirculation within grooved substrates regulates cell positioning and cell docking inside microfluidic channels. Lab on a Chip. 8(5): 747-754 (2008).

Mannino, R.G., et al. Endothelial cell culture in microfluidic devices for investigating microvascular processes. Biomicrofluidics 12(4): 042203 (2018).

Mouchaers, K.T.B., et al. Fasudil reduces monocrotaline-induced pulmonary arterial hypertension: comparison with bosentan and sildenafil. European Respiratory Journal. 36(4):800-807 (2010). DOI: 10.1183/09031936.00130209.

Myers, D.R., et al. Endothelialized microfluidics for studying microvascular interactions in hematologic diseases. J Vis Exp. 64 (2012).

Nguyen, T., et al. A Complete Protocol for Rapid and Low-Cost Fabrication of Polymer Microfluidic Chips Containing Three-Dimensional Microstructures Used in Point-of-Care Devices. Micromachines (Basel) 10(9) (2019).

Nguyen, T., et al. Multicellular Cell Seeding on a Chip: New Design and Optimization towards Commercialization. Biosensors 12:587 (2022) https://doi.org/10.3390/bios 12080587.

Nguyen, T., et al. Point-of-care devices for pathogen detections: The three most important factors to realize towards commercialization. TrAC Trends in Analytical Chemistry 131: 116004 (2020).

Nicolls, M.R., et al. The Roles of Immunity in the Prevention and Evolution of Pulmonary Arterial Hypertension. Am J Respir Crit Care Med 195(10): 1292-1299 (2017).

Oka, M., et al. Rho Kinase-Mediated Vasoconstriction Is Important in Severe Occlusive Pulmonary Arterial Hypertension in Rats. American Heart Association. Circulation Research. 100:923-929 (2007) DOI: 10.1161/01.RES.0000261658.12024.18.

Olanrewaju, A., et al. Capillary microfluidics in microchannels: from microfluidic networks to capillaric circuits. Lab Chip 18: 2323-2347 (2018).

Rabinovitch. M. Molecular pathogenesis of pulmonary arterial hypertension. The Journal of Clinical Investigation. 122 (12): 4306-4313 (2012).

Ranchoux, B., et al. Endothelial-to-Mesenchymal Transition in Pulmonary Hypertension. Downloaded from http://circ.ahajournals.org/ on Jan. 20, 2015.

Rashid, J., et al. Fasudil and DETA NONOate, Loaded in a Peptide-Modified Liposomal Carrier, Slow PAH Progression upon Pulmonary Delivery. Mol Pharm. 15(5):1755-1765 (2018) DOI: 0.1021/acs.molpharmaceut.7b01003.

Reusch. P.H., et al. Activation of JNK/SAPK and ERK by Mechanical Strain in Vascular Smooth Muscle Cells Depends on Extracellular Matrix Composition. Biochemical and Biophysical Research Communications. 237(2):239-244 (1997).

Roman, B.L., et al. Catching a Disease: A Molecular Trap as a Therapy for Pulmonary Arterial Hypertension. American Journal of Respiratory and Critical Care Medicine. 194(9):1047-1049 (2016).

Sa, S., et al. Induced Pluripotent Stem Cell Model of Pulmonary Arterial Hypertension Reveals Novel Gene Expression and Patient Specificity. Am J Respir Crit Care Med 195(7):930-941 (2017).

Sheikh, A., et al. Recapitulation of developing artery muscularization in pulmonary hypertension. Cell Rep. 6(5):809-817 (2014) DOI: 10.1016/j.celrep.2014.01.042.

Shin, Y. et al. Microfluidic assay for simultaneous culture of multiple cell types on surfaces or within hydrogels. Nat Protoc. 7(7):1247-1259 (2012) DOI: 10.1038/nprot.2012.051.

Stenmark. K.R., et al. Animal models of pulmonary arterial hypertension: the hope for etiological discovery and pharmacological cure. Am J Physiol Lung Cell Mol Physiol 297:L1013-L1032 (2009) DOI: 10.1152/ajplung.00217.2009.

Stenmark. K.R., et al. Endothelial-to-Mesenchymal Transition: An Evolving Paradigm and a Promising Therapeutic Target in PAH. Circulation. 133(18): 1734-1737 (2016) DOI: 10.1161/CIRCULATIONAHA.116.022479.

Sutendra. G., et al. Pulmonary Arterial Hypertension: Challenges in Translational Research and a Vision for Change. Science Translational Medicine. 5(208):1-14 (2013) Downloaded from stm.sciencemag.org on Mar. 16, 2015.

Umar. S., et al. Estrogen Rescues Preexisting Severe Pulmonary Hypertension in Rats. American Journal of Respiratory and Critical Care Medicine. 184:715-723 (2011).

Xu, S., et al. Development and Characterization of In Vitro Microvessel Network and Quantitative Measurements of Endothelial [Ca2+]i and Nitric Oxide Production. J Vis Exp. 111(2016).

Zaiman. A., et al. One Hundred Years of Research in the Pathogenesis of Pulmonary Hypertension. Am J Respir Cell Mol Biol. 33:425-431 (2005) DOI: 10.1165/rcmb.F307.

Zervantonakis, I.K., et al. Three-dimensional microfluidic model for tumor cell intravasation and endothelial barrier function .. PNAS 109(34):13515-13520 (2012).

Zhang, Y., et al. Effects of fasudil on pulmonary hypertension 1 in clinical practice. Pulmonary Pharmacology & Therapeutics (2017) DOI: 10.1016/j.pupt.2017.08.002.

\* cited by examiner

EMULATING DISEASE IN A MICROFLUIDIC SYSTEM WITH A RELEASABLE INTERFACIAL FILM AND COMMUNICATION BETWEEN NON-GEL AQUEOUS SOLUTIONS

CROSS-REFERENCE TO RELATED APPLICATIONS

This application is a divisional of U.S. patent application Ser. No. 17/865,021, filed Jul. 14, 2022, which claims the benefit of U.S. Provisional Application No. 63/226,733, filed Jul. 28, 2021, each of which is hereby incorporated herein by reference in it's entirety.

BACKGROUND

Field of the Invention

The teachings herein are directed to multilayer microfluidics systems and methods, namely a modified microfluidics chip that separates tissue types before allowing a controlled contact through release of an interfacial film created between pillars, and methods for using the devices in providing treatments of diseases, including a personalized medicine approach.

Description of the Related Art

For improving treatment of disease, investigators have used various animal studies to develop treatments for disease. The problem is that animals often do not effectively mimic human pathophysiology, and only partially emulate important pathological changes of humans. Moreover, a variety of animal species are used in a variety of disease-producing agents or environments, representing a great deal of variability in the disease severity, progression, and response to therapies. The influence of any of a variety of factors are not well-represented by animal studies, and the influence of this variety of factors affect how we treat disease. Such factors can include, for example, the biological sex of the subject treated, including the influence of sex hormones, especially the role of estrogen. A better understanding of how these factors affect treatments allow for improvements in the development of sex-based therapies, for example.

Microfluidic devices have been used to construct representations of physiologically-relevant tissue and organ level functions and disease. Prior art microfluidic devices use a single channel in which to seed and grow a type of cell, and these single channel devices are limited in application. For example, a single channel device cannot represent interactions between different types of cells including, but not limited to, layered vascular tissue.

Developing an effective multilayer system involves the challenges of creating and maintaining the integrity of adjacent cellular layers. The multilayer systems must provide a realistic interaction between the layers that is a controllable interaction. Some prior art microfluidic devices have tried to use a gel to maintain the integrity of the cellular layer, but interaction between layers is not realistic, as gels are not present physiologically and change the rate of the interactions that can occur and, as such, the amount of control over the interaction is limited by the presence of the gel. One of skill will appreciate that mammalian cells are not transported or send signals in the body through a gel, and so the use of a gel is not a true physiologic condition.

For at least the above reasons, the skilled artisan will appreciate having a microfluidic device that can more realistically represent true physiologic conditions in the development of a treatment for disease, particularly diseases that involve a plurality of tissue types that normally interact as layers of tissue. Such microfluidics systems can allow, for example, for a construction of cellular interactions that occur in a select pathological process. In some cases, the systems provided herein can be constructed such that cells from one channel can readily send cues to cells in neighboring channels to represent more accurate pathological conditions in the development of a treatment. In some cases, the systems provided herein can allow diseased cells in their channel to communicate with healthy cells in a neighboring channel. In some cases, the systems provided herein can allow healthy cells to become sick to generate data about the cellular interaction in the particular pathological process in order to develop an effective treatment. In some cases, the systems provided herein can show the effect of drug treatments on a disease including relative changes in drug selection, drug dose, drug tolerance, drug half-life, and the like. One of skill will readily appreciate that there are a plethora of other variables that can be introduced using the systems and methods provided herein to develop treatments, including prophylactic treatments to inhibit or prevent the onset of disease, treatments that inhibit a pathological process after onset, and treatments that ameliorate the symptoms of disease.

Accordingly, and for at least the above reasons, those of skill in the art will appreciate microfluidics systems and methods that provide more accurate, aqueous, physiological conditions as a way (i) to control the cellular interactions that occur; (ii) to develop treatments based on the cellular interactions; (iii) to introduce variables of interest in the development of treatments, the variables affecting the pathological processes; (iv) to test therapies, including drugs, radiation, or a combination thereof; and, (v) to identify variables that affect treatments in a subject, for example, cellular transport and signaling mechanisms that are relevant in the treatment of a disease.

SUMMARY

Systems and methods are provided to assist in developing treatments for disease. The systems and methods can include a precision medicine approach for any disease, and can include a personalized medicine approach for an individual. The systems and methods include the use of microfluidic devices that can be used to reconstruct the tissue interactions in a disease process. The reconstruction can include an interaction of a plurality of cell types, interaction between cellular layers in tissue, or a combination of these cellular interactions. The interaction provides information on relevant cellular communications in a disease state to design a treatment, as well as information on the effect of a particular type of treatment or treatment combinations such as, for example, a drug therapy, radiation therapy, or a combination thereof. Aqueous interfacial films are used to provide control over tissue interaction, the films remaining intact for the formation of a cellular layer but releasing when desired to allow for interaction between the cell "layers" in adjacent channels. The interfacial films provide control over the release while avoiding the slow transport that is otherwise present when using a hydrogel to stabilize tissue layers.

In some embodiments, a microfluidics system designed for emulating cellular physiologies in a subject is provided. The system can comprise a microfluidic chip and a first channel adjacent to a second channel. In these embodiments, the first channel and the second channel are connected to the chip and include a first port configured for injection of a first aqueous cell culture media into the first channel; a second port configured for injection of a second aqueous cell culture media into the second channel; and, a first wall with openings, the first wall shared by the first channel and the second channel, and the openings in the first wall configured to (i) form a temporary/releasable, first aqueous interfacial film across the openings of the first wall upon the injection of the first aqueous cellular solution and (ii) allow for a cellular communication to occur between the first channel and the second channel upon a release of the first interfacial film from the openings.

The interfacial film needs to release to enable communication between cells in adjacent channels. In some embodiments, the injection of the second aqueous cellular solution causes the release of the first interfacial film from the openings.

The wall with openings needs to be configured to establish the interfacial film with sufficient stability to maintain the integrity of a cellular layer in the respective channel long enough to create the emulated tissue structure. In some embodiments, the interfacial film can be formed from the injection of any of the aqueous solutions. In some embodiments, the wall is configured to establish the first interfacial film across the openings when injecting the first aqueous cellular solution. In some embodiments, the openings include a hydrophobic material to establish the first interfacial film across the openings of the first wall when injecting the first aqueous cellular solution. In some embodiments, the openings are outlined by opposing wedge-shaped edges that share a plane in order to establish the first interfacial film across the openings when injecting the first aqueous cellular solution. In some embodiments, the openings include a shape selected from the group consisting of circles and ovals. In some embodiments, the openings are outlined by polygonal-shaped structures, the structures providing opposing edges on at least two opposing sides of the opening, wherein the opposing edges share a plane in order to establish the first interfacial film across the openings of the first wall when injecting the first aqueous cellular solution. In some embodiments, the openings of the first wall are the spaces between adjacent columns along a series of columns; wherein, each column in the series of columns has a central axis that is at least substantially normal to the chip, each pair of adjacent columns provides a pair of opposing edges that share a plane in order to establish the first interfacial film across the openings of the first wall when injecting the first aqueous cellular solution.

In some embodiments, the systems can include three or more different cell types to emulate more complex tissue structures. In these embodiments, the systems further comprise a third channel; and, a third port configured for injection of a third aqueous cellular solution into the third channel. The systems include a second wall with openings, the second wall shared by the second channel and the third channel, and the openings in the second wall configured to (i) form a temporary, second aqueous interfacial film across the openings of the second wall upon the injection of the third aqueous cellular solution and (ii) allow for a cellular communication to occur between the second channel and the third channel upon a release of the interfacial film from the openings.

The systems can be designed with separate injection ports and channels that can be used to feed the cells with growth media and administer a drug to test the response of the emulated tissue structure to the drug. As such, in some embodiments, the system can further comprise a growth medium channel having a growth medium port. The interfacial film can comprise the growth medium.

Likewise, the systems can be designed for multiple growth medium ports, each for supplying cell media to feed the cells and a select drug to test. As such, in some embodiments, the systems can further comprise a first growth medium channel having a first growth medium port and located in communication with the first channel and a second growth medium channel having a second growth medium port and located in communication with the second channel.

The systems are designed to represent the physiologic environment of a diseased tissue. As such, in some embodiments, a method of emulating a disease in a subject is provided. The methods can comprise obtaining one of the systems taught herein; injecting the first aqueous cellular solution into the first channel to introduce a first cell of the disease, the injecting forming the temporary, first aqueous interfacial film across the openings of the first wall; and, injecting the second aqueous cellular solution into the second channel to introduce a second cell of the disease. In these embodiments, the first interfacial film releases after the injecting of the second aqueous solution; and, the first cell and the second cell communicate after the releasing of the first interfacial film to emulate the disease state. These methods can further comprise the steps of injecting a drug to the system to identify a suitable drug, identify a suitable dosage, and/or identify a desired activity of a drug; and administering the drug to a subject in need of the treatment.

In some embodiments, the system chosen has at least three channels, and at least three different cell types in the emulated tissue structure. As such, in some embodiments, the method of emulating a disease comprises obtaining a system having at least three channels; injecting the first aqueous cellular solution into the first channel to introduce a first cell of the disease, the injecting forming the temporary, first aqueous interfacial film across the openings of the first wall; injecting the third aqueous cellular solution into the third channel to introduce a third cell of the disease, the injecting forming the temporary, second aqueous interfacial film across the openings of the second wall; and, injecting the second aqueous cellular solution into the second channel to introduce a second cell of the disease. In these embodiments, the first interfacial film releases after the injecting of the second aqueous solution; the second interfacial film releases after the injecting of the second aqueous solution; the first cell and the second cell communicate after the releasing of the first interfacial film to emulate the disease state; and, the second cell and the third cell communicate after the releasing of the second interfacial film to emulate the disease state. These methods can further comprise the steps of injecting a drug to the system to identify a suitable drug, identify a suitable dosage, and/or identify a suitable activity; and administering the drug to a subject in need of the treatment.

In some embodiments, a gel can added between layers, to further stabilize the integrity of those layers, particularly between layers of a system where a controllable release of an interfacial film is not needed or, in some embodiments, not desired. This may be useful in applications where stable layer separation is needed, for example. As such, in some embodiments, the method of emulating a disease in a subject can comprise obtaining a system having at least three channels; injecting the first aqueous cellular solution into the first channel to introduce a first cell type of the disease, the injecting forming the temporary, first aqueous interfacial film across the openings of the first wall; injecting the third aqueous cellular solution into the third channel to introduce a third cell type of the disease, the injecting forming the temporary, second aqueous interfacial film across the openings of the second wall; and, injecting the second aqueous cellular solution into the second channel in the form of an aqueous gel to introduce a second cell of the disease. In these embodiments, the first interfacial film releases after the injecting of the second aqueous solution; the second interfacial film releases after the injecting of the second aqueous solution; the first cell and the second cell communicate after the releasing of the first interfacial film to emulate the disease state; and, the second cell and the third cell communicate after the releasing of the second interfacial film to emulate the disease state. These methods can further comprise the steps of injecting a drug to the system to identify a suitable drug, identify a suitable dosage, and/or identify a suitable activity; and administering the drug to a subject in need of the treatment.

The methods of emulating a tissue structure, and emulating a disease, lead naturally to methods of treating the diseased tissue structure. As such, methods of treating an emulated disease with a drug are provided. The methods can include constructing a representation of a disease as taught herein; selecting a drug candidate to treat the disease; injecting/administering the drug in any one of the channels; and, observing the drug activity. In some embodiments, the drug can be administered in the first channel or the second channel. In some embodiments, the drug can be administered in the first channel, the second channel, or the third channel. These methods can further comprise the steps of injecting a drug to the system to identify a suitable drug, identify a suitable dosage, and/or identify a suitable activity; and administering the drug to a subject in need of the treatment.

Various types of diseases can be emulated and treated using the systems and methods provided herein. In some embodiments, the methods are directed to treating an emulated vascular disease with a drug. In these embodiments, the methods can include obtaining a system taught herein, the system having at least three channels for the introduction of three vascular cell types; injecting the first aqueous cellular solution into the first channel to introduce a first cell of the disease to form an adventitial cell layer, the injecting forming the temporary, first aqueous interfacial film across the openings of the first wall; injecting the third aqueous cellular solution into the third channel to introduce a third cell of the disease to form an endothelial cell layer, the injecting forming the temporary, second aqueous interfacial film across the openings of the second wall; and, injecting the second aqueous cellular solution into the second channel to introduce a second cell of the disease to form a smooth muscle layer. These methods further comprise selecting a drug; and, administering the drug to the first growth medium channel or the second growth medium channel. In these embodiments, the first interfacial film releases after the injecting of the second aqueous solution; the second interfacial film releases after the injecting of the second aqueous solution; the first cell and the second cell communicate after the releasing of the first interfacial film to emulate the disease state; and, the second cell and the third cell communicate after the releasing of the second interfacial film to emulate the disease state. These methods can further comprise the steps of injecting a drug to the system to identify a suitable drug, identify a suitable dosage, and/or identify a suitable activity; and administering the drug to a subject in need of the treatment.

DETAILED DESCRIPTION OF THE INVENTION

Figure 1:
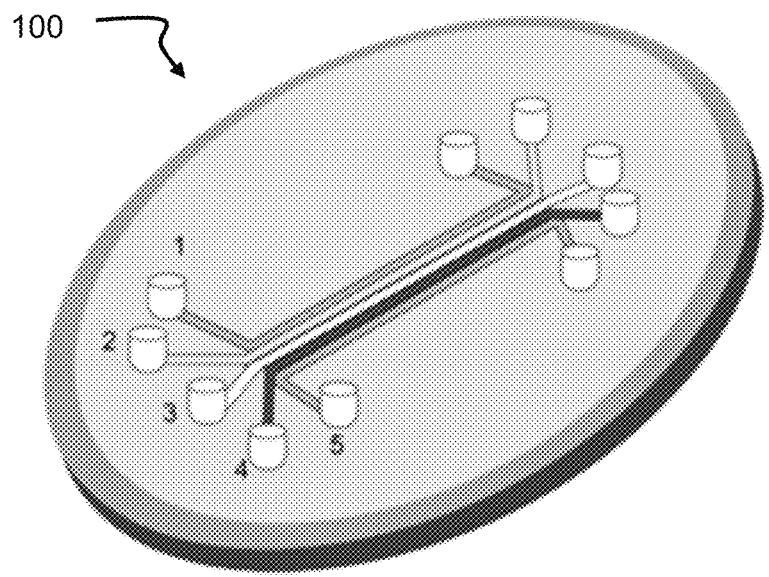
FIG. 1 shows an illustration of the microfluidics chip, according to some embodiments.

The teachings herein are generally directed to systems and methods for creating and using a microfluidic device with multiple channels having a releasable layer. The devices include a modified microfluidics chip that separates tissue types before allowing a controlled contact through release of an interfacial film, and methods for using the devices in providing treatments for diseases, such treatments including a personalized medicine approach, in some embodiments.

One of skill will appreciate that the devices can be used to develop a treatment plan, in some embodiments. The devices can seed and grow multiple cell types in the system to provide an improved representation of a physiologic system. In some embodiments, the systems and methods represent complex pathological processes for use in the development of a treatment. The term "interfacial" refers to one side being exposed to air and the other side exposed to fluid, for example, a cell growth media such as an aqueous, fluid cell growth media. The term "subject" and "patient" can be used interchangeably and refer to an animal such as a mammal including, but not limited to, non-primates such as, for example, a cow, pig, horse, cat, dog, rabbit, rat and mouse; and primates such as, for example, a monkey or a human.

In some embodiments, the development of a treatment can include identifying a drug having the desired activity, dosage, half-life, and/or tolerance, or a combination thereof, in a subject for a treatment/The systems and methods can be used, for example, to identify the optimal dosage of a drug(s) for a treatment, the efficacy of a select drug(s) for a treatment, alone or in combination, the stability of a drug for a treatment, the patient sensitivity/tolerance of a drug(s) for a treatment, and in the identification of a drug formulation(s) for a treatment. Drug formulations can include, for example, the use of nanoparticles, coatings, targeting moieties, drug delivery complexes, and combinations thereof. One of skill will appreciate that the systems and methods provided herein can be used in precision medicine, and in personalized medicine, leading to the development of improved treatments, such as an individualized treatment that is tailored to a subject's age, sex, race, known allergies, and the like.

The development of treatments can include using the systems and methods to represent the communication between cells that occurs in any system of the body. In some embodiments, the system of the body can be selected from the circulatory system, the cardiovascular system, the digestive system, the excretory system, the endocrine system, the exocrine system, the integumentary system, the immune system, the lymphatic system, the musculature system, the nervous system, the renal system, the urinary system, the reproductive system, the respiratory system, the skeletal system, or a combination thereof. Each of these physiologic systems suffers its own pathological diseases and problems, many of which are well-known to those of skill, and the systems and methods taught herein can be used to create a more realistic physiologic environment for diseases that can occur in each of these systems, identify factors that can affect treatment, such as age, sex, hereditary factors, and the presence of other physiologic conditions, such as additional diseases or disorders present in the subject. In some embodiments, the systems and methods can be designed to also represent the presence of other therapies, including primary therapies, adjuvant therapies, and the like, which can affect a treatment. For example, a subject may be undergoing chemotherapy while also undergoing radiation therapy, and the subject may also have additional genetic factors or disease states that can affect the development of a treatment.

A valuable contribution of the systems and methods taught herein, include the ability to construct tissue systems with separate, discrete tissue layers while providing control over the interaction between the tissue layers. The interfacial films taught herein can be used to isolate the tissue layers from each other before triggering a controlled contact of the tissue layers. Any organ system can be represented, and a treatment for any disease can be pursued, established, and used on a subject, particularly where the disease implicates multiple cell layers, like vascular tissues, immune tissues, cancer tissues, and the like. Treatments for diseases that involve, for example, angiogenesis, inflammatory response, wound healing, drug response, metastasis of cancer cells between organs, and the like, can be identified and administered to a subject in need.

In some embodiments, the systems and methods can be particularly suited to represent a vascular disease, develop a treatment for a vascular disease. A method of treatment is provided, the method including constructing a system to represent a vascular disease, identifying a drug for treating the vascular disease using the system, and administering the drug to treat the vascular disease. The identifying of the drug can include identifying the amount of the drug, the half-life of the drug, the efficacy of the drug, and the tolerance of the drug in the subject. The vascular system can be constructed with smooth, adventitial, and endothelial cells, as each of these cells can be implicated in a vascular disease. The method can include selecting a cell growth media suitable for a smooth, adventitial, and endothelial cell growth. One of skill will appreciate that the cell growth media can be selected to support smooth, adventitial, and endothelial cells.

In some embodiments, treatments for atherosclerosis can be developed. In some embodiments, treatments for any disease that includes endothelial dysfunction can be developed, such as those diseases that can result from diabetes or metabolic syndrome, hypertension, smoking, and physical inactivity. Such treatments can promote a healthy endothelium, which not only arbitrates endothelium-dependent vasodilation, but also actively suppresses thrombosis, vascular inflammation, and hypertrophy. As such, in some embodiments, the treatments developed can be used to treat thrombosis, vascular inflammation, and hypertrophy.

In some embodiments, treatments for cancer be developed using the systems methods herein. Such treatments can be a vascular disease treatment, as angiogenesis, or the inhibition of angiogenesis, as a mechanism related to cancer and cancer treatments. Angiogenesis inhibiting drugs can be used, for example, to inhibit or stop growth of blood vessels that feed cancer tissue growth. And, similarly, treatments for wound healing can be developed, as directed to the use of drugs that increase angiogenesis to improve blood flow to tissue healing treatments. Treatments for sarcoidosis, sclerosis, and coagulation disorders can all be developed using the systems and methods taught herein.

In some embodiments, the cancer treatment can be for solid tumors or liquid tumors, such as lymphomas, and leukemias. In some embodiments, the leukemia treatment is for acute myeloid leukemia (AML). In some embodiments, the systems and methods taught herein can be used to represent the physiologic environment of any cancer, stage of cancer, metastasis of the cancer between tissues, and the like, in order to develop a cancer treatment.

The Releasable Interfacial Layer

A component of the system that provides control over the separation of tissue layers and intermixing of tissue layers is what is referred to herein as a "releasable interfacial layer" or "interfacial layer" or "interfacial film". It can also be referred to as a "temporary" interfacial layer or interfacial film. Such terminology can be used interchangeably. The interfacial layers can be created as a component of one or more walls that separate independent tissue channels. In some embodiments, the systems and methods use a single interfacial layer to separate tissue layers or channels. In some embodiments, the systems and methods use a plurality of interfacial layers to separate tissue layers or channels. In some embodiments, the systems can have 2 interfacial layers, one on each side of a channel that separates tissue layers or channels. The walls separating the independent tissue channels are comprised of pillars, and an interfacial layer is created between each adjacent pillar, spanning between pillars.

Cell media is used as a carrier for each of the tissue layers. Cell media can be referred to as "cell growth media", "cell culture media", or "cell growth culture media". It should be appreciated that the cell growth media can be a nutrient media, a culture media, a minimal media, a selective media, a differential media, a transport media, or an enriched media. Liquid media can be referred as a "broth" in some embodiments. As such, in some embodiments, the interfacial layers can be comprised of the growth media which can include, for example, aqueous, liquid cell culture growth media which can be referred to in some embodiments as "aqueous, liquid cell growth media". Such media can be used to create a releasable, interfacial layer. An example cell growth media is rat tail type I collagen solution. In some embodiments, any cell growth media having a collagen concentration ranging from 10% to 35% collagen can be used. In some embodiments, the collagen concentration can be 10%, 15%, 20%, 25%, 30%, 35%, or any amount therein in increments of 1%. In some embodiments, the collagen concentration of the cell media is 20%, 21%, 22%, 23%, 24%, 25%, 26%, 27%, 28%, 29%, 30%, or any amount therein in increments of 0.1%.

However, the systems and methods can also include a semi-solid cell growth media, in some embodiments. In some embodiments, the semi-solid cell growth media can be a hydrogel. One of skill will appreciate that any suitable hydrogel, cell growth media can be used, such as a collagen based hydrogel cell growth media.

The skilled artisan can identify a suitable cell growth media that is appropriate for a particular tissue application. In some embodiments, the cell growth media can be referred to as a "physiologic media", a chemically defined culture media that is intended to provide controlled cell culture condition, for example, to emulate the composition of blood or other physiologic environments needed to represent a physiologic condition. In some embodiments, the cell growth media can be a Basal Medium Eagle (BME), a Minimal Essential Medium (MEM), Dulbecco's Modified Eagle Medium (DMEM), Roswell Park Memorial Institute (RPMI) 1640, McCoy's 5A Modified Medium, cell culture medium for a specific cell type such as SmGM™-2 Smooth Muscle Cell Growth Medium-2 BulletKit™, EGM™-2 MV Microvascular Endothelial Cell Growth Medium-2 Bullet-Kit™ and COMPLETE FIBROBLAST MEDIUM/W KIT—500 ML and the like.

The interfacial layers can provide control in some embodiments because they are controllably releasable. By "controllably releasable", we mean that the interfacial film is sufficiently stable to remain in place until an aqueous fluid is placed in contact with the "air side" of the interfacial film, thus releasing the film containing the cell tissue in the channels and allowing the channels and their respective cell tissues to communicate. In some embodiments, the interfacial layer can be released upon introduction of an aqueous solution in a channel adjacent to the channel in which the film was formed, such as an adjacent channel. In contrast, in some embodiments, the integrity of the channel can be prolonged, if desired, by introducing a first aqueous cellular solution in a first channel and introducing a second aqueous cellular solution in a second channel in the form of a gel, where the gel maintains the integrity of the first cellular layer formed in the first channel and the second cellular layer formed in the second channel. It should be appreciated, however, that a gel in this layered combination of cells does not truly represent the actual aqueous cellular environments in a mammal. It may be desired to simply stabilize that part of the representative layered system of cells, whereas the other part of the representative system contains a releasable interfacial film. In some embodiments, the first layer can be an aqueous solution, the adjacent second layer can be an aqueous gel, and the third layer can be an aqueous solution, for example. In some embodiments, the layers can have alternating aqueous cell media—aqueous gel—aqueous cell media structures, for example.

The interfacial films are a technical feature that provide a controllably releasable mechanism that serves as a barrier between the cell layers or channels. It should be appreciated that, in some embodiments, the tissue structures represented by the systems and methods can have a laminar orientation between the cell layers, and it is desired to maintain the integrity of the cellular layer structure that is created in the seeding phase. However, the interfacial film between the layers can be later released, when desired, to allow for a representative physiological communication between the layers.

FIG. 1 shows an illustration of a microfluidics chip, according to some embodiments. Microfluidics chip 100 has 5 channels 1, 2, 3, 4, 5. Channels 2, 3, and 4 are for introduction of 3 different types of cells to emulate a tissue. Channels 1 and 5 are added for adding growth medium to feed the cells to prolong the life of the cells, and these channels can also serve as growth media reservoirs that can be changed periodically, as needed.

Figure 2:
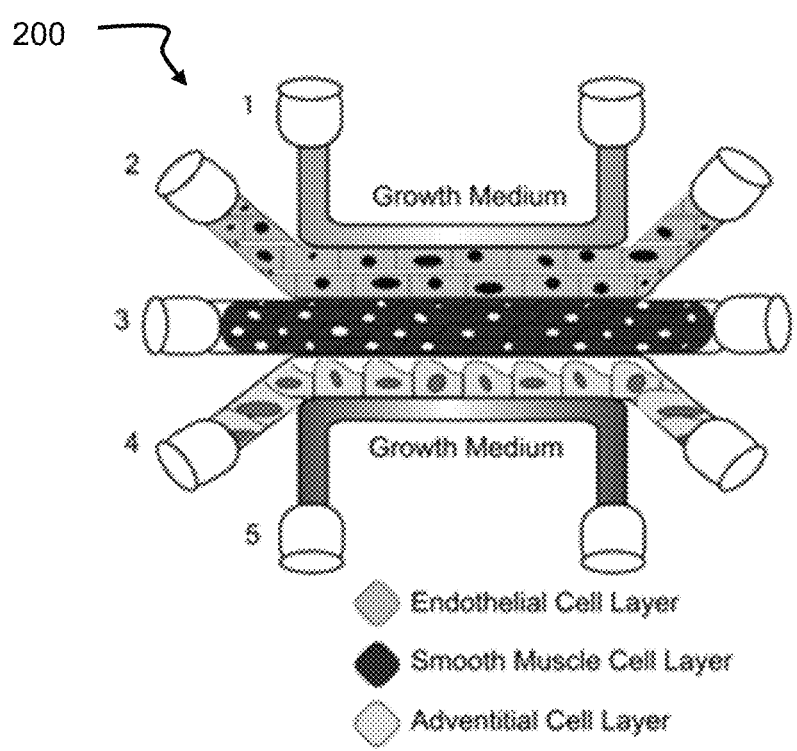
FIG. 2 illustrates a vascular tissue structure formed on a chip in channels, according to some embodiments.

The systems and methods taught herein can use the multiple channels to represent any layered tissue structure and develop a treatment for any disease process. FIG. 2 illustrates a vascular tissue structure formed on a chip in channels, according to some embodiments. Emulated tissue 200 shows channels 1-5. Channel 2 contains the endothelial cells to emulate an endothelial cell layer, channel 3 contains smooth muscle cells to emulate a smooth muscle cell layer, and channel 4 contains adventitial cells to emulate an adventitial cell layer, the combination of which emulates a vascular structure. And, as discussed, channels 1 and 5 are configured for adding growth medium to feed the cells to prolong the life of the cells.

In some embodiments, channels 1 and 5 can also serve as growth media reservoirs that can be changed periodically, as needed, so that the systems and methods can operate over an extended period of time. In some embodiments, the period of time can be 1 hour, 2 hours, 3 hours, 4 hours, 5 hours, 6 hours, 7 hours, 8 hours, 9 hours, 10 hours, 11 hours, 12 hours, 18 hours, 24 hours, 2 days, 3 days, 4 days, 5 days, 6 days, 7 days, 8 days, 9 days, 10 days, 11 days, 12 days, 13 days, 14 days, or any period or range of time therein in increments of 1 min.

In some embodiments, channels 1 and 5 can serve as ports to administer drugs to the tissue in a liquid aqueous growth media. Such a system can be used to identify drug type, drug dosage, drug stability, and drug tolerance, in some embodiments.

In some embodiments, channels 1 and/or 5 can be used to administer hydrostatic pressure. Such a pressure administration can be used, for example, to emulate blood pressure changes and effects of stress on the vessels. This can help develop a treatment for subjects having a range of blood pressures, for example. Any mechanism of pressure known to one of skill to be suitable can be used in the addition of pressure, such as a peristaltic pump.

Figure 3:
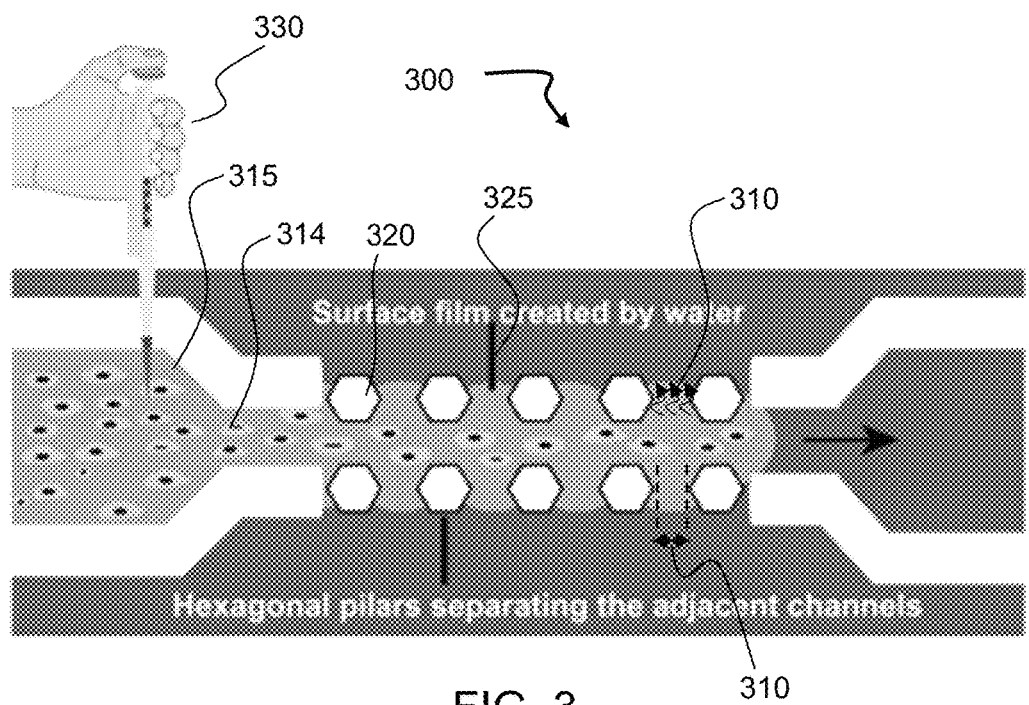
FIG. 3 illustrates a top view of a channel of a device, the channel having a "discontinuous wall", which is a wall with openings between pillar-type structures that compose a part of a channel, according to some embodiments.

FIG. 3 illustrates a top view of a channel of a device, the channel having a "discontinuous wall", which is a wall with openings between pillar-type structures that compose a part of a channel, according to some embodiments. Channel 300 includes a wall 305 with openings 310, the wall being shared with an adjacent channel (not shown), so that first cells 314 in a first aqueous cellular solution 315 can communicate with second cells (not shown) in a second aqueous cellular solution (not shown) to emulate the communication between the first cells and the second cells in an emulated tissue structure. Prior to the communication, however, the emulated tissue structure needs to be created, and so the integrity of each cell layer needs to be maintained. Maintaining the integrity of each cell layer during formation of the tissue structure is facilitated by the creation of a temporary, aqueous interfacial film 325 across the openings 310 through the aqueous surface tension created by the contact between the first aqueous cellular solution 315 with columns 320. The process of creating the cell layer can be referred to as "seeding" 330 which can be done manually by hand, or automatically through a pump in the system.

The microfluidics devices taught herein are uniquely designed to provide temporary, free-standing aqueous interfacial films between channels. In fact, the interfacial films are a component of the channels, and serve to initially maintain the integrity of the channels during the formation of the emulated tissue structure. The temporary interfacial film allows for the temporary formation of channel that can accept a first cell type that is contained by the interfacial film while another channel, also having an interfacial film as a component, accepts a second cell type. After the passage of time, the interfacial films release, and the cells can communicate between adjacent channels that were once separated by the interfacial films. In some embodiments, these temporary interfacial films can be referred to as "sacrificial walls" that first hold the cellular layers in place and then allow for communication between the cells upon release of the interfacial film, the sacrificial walls creating a separation that represents cellular arrangements that exist in the body and ultimately releasing when desired to allow the cells to communicate.

The pillars can have any configuration desired, the configuration affecting the interfacial film in some embodiments. The pillars can be configured with edges that oppose each other, preferably on the same plane, in order to create the desired interfacial film between the pillars and contain the cellular layer that is being created in the channel. The pillars can have a hexagonal footprint, as shown in FIG. 3, for example. The hexagonal cylinder, as noted, should have edges oriented point-to-point and preferably on the same plane. The aqueous, interfacial film forms a temporary wall that maintains the integrity of the cell layer during seeding of the channel, and then the interfacial layer releases to allow the cells communicate.

In some embodiments, hydrophilic materials are not used to form the pillars, as the hydrophilic materials may not create a stable interfacial film with the cell culture media.

One of skill will appreciate that, in some embodiments, the pillars can have a cross-section that is round, elliptical, polygonal, or a combination thereof. In some embodiments, the polygonal shape is 3-sided, 4-sided, 5-sided, 6-sided, 7 sided, 8-sided, 9-sided, 10-sided, 11-sided, or 12-sided. In some embodiments, the pillar is a cylinder. In some embodiments, the pillar is a round cylinder. In some embodiments, the pillar is an elliptical cylinder. In some embodiments, the pillar is a polygonal cylinder, like the hexagonal cylinder in FIG. 3.

The openings 310 are defined by the distance between pillars, a "bridging distance" for an interfacial film of the systems and methods taught herein. The distance between pillars can also be referred to as an "interpillar distance", a device design feature that should be carefully configured to range from 30 uM to 250 uM. The lower end of the range at 30 uM is limited by the size of the cell tissue, whereas the upper end of 250 uM is limited by the stability of the interfacial film.

In some embodiments, the interpillar distance can range from 30 uM to 200 uM, 30 uM to 100 uM, or any range therein in increments of 1 uM. In some embodiments, the interpillar distance can be about 25 uM, 30 uM, 35 uM, 40 uM, 45 uM, 50 uM, 55 uM, 60 uM, 65 uM, 70 uM, 75 uM, 80 uM, 85 uM, 90 uM, 100 uM, 105 uM, 110 uM, 115 uM, 120 uM, 125 uM, 130 uM, 135 uM, 140 uM, 145 uM, 150 uM, 155 uM, 160 uM, 165 uM, 170 uM, 175 uM, 180 uM, 185 uM, 190 uM, 195 uM, 200 uM, 215 uM, 220 uM, 225 uM, 230 uM, 235 uM, 240 uM, 245 uM, 250 uM, 255 uM, 260 uM, or any distance or range of distances therein in increments of 1 uM.

The interpillar distance is dictated by the ability to form an interfacial film between pillars with the cell culture media used in the systems and methods taught herein. And, since the pillar height is also restricted by similar surface tension constraints, the pillar height also forming a bridging distance for the interfacial films, the pillar height can be also about 25 uM, 30 uM, 35 uM, 40 uM, 45 uM, 50 uM, 55 uM, 60 uM, 65 uM, 70 uM, 75 uM, 80 uM, 85 uM, 90 uM, 100 uM, 105 uM, 110 uM, 115 uM, 120 uM, 125 uM, 130 uM, 135 uM, 140 uM, 145 uM, 150 uM, 155 uM, 160 uM, 165 uM, 170 uM, 175 uM, 180 uM, 185 uM, 190 uM, 195 uM, 200 uM, 205 uM, 210 uM, 200 uM, 215 uM, 220 uM, 225 uM, 230 uM, 235 uM, 240 uM, 245 uM, 250 uM, 255 uM, 260 uM, or any distance or range of distances therein in increments of 1 uM. As with the interpillar distance, the pillar height is also a device design feature that should be carefully configured to range from 30 uM to 250 uM. In some embodiments, the pillar height can range from 30 uM to 200 uM, 30 uM to 100 uM, or any range therein in increments of 1 uM.

In some embodiments, a multichannel microfluidics device can have 3 channels. In some embodiments, a multichannel microfluidics device can have 2, 3, 4, 5, 6, 7, 8, 9, 10 or more channels. In some embodiments, the user preselects a device that is designed to have either 2, 3, 4, 5, 6 or more channels. In many embodiments, the multi-channel device allows each of the cells to be grown in it's own respective channel among a plurality of channels, each channel communicating with at least one neighboring channel in the plurality of channels, and each cell type staying within it's respective channel in the seeding stage but communicating by cellular signaling mechanisms, which can include, for example, paracrine signaling, which does not involve cellular contact, and juxtacrine signaling, which is ligand-receptor binding that does involve cellular contact. This arrangement can allow for a wide variety of configurations to be chosen and designed for use in emulating the cellular communications in a pathological process.

As such, in some embodiments, a microfluidics system designed for emulating cellular physiologies in a subject is provided. The system can comprise a microfluidic chip; and, a first channel adjacent to a second channel. In these embodiments, the first channel and the second channel are connected to the chip and include a first port configured for injection of a first aqueous cellular solution into the first channel; a second port configured for injection of a second aqueous cellular solution into the second channel; and, a first wall with openings, the first wall shared by the first channel and the second channel, and the openings in the first wall configured to (i) form a temporary, first aqueous interfacial film across the openings of the first wall upon the injection of the first aqueous cellular solution and (ii) allow for a cellular communication to occur between the first channel and the second channel upon a release of the first interfacial film from the openings.

The interfacial film needs to release to enable communication between cells in adjacent channels. In some embodiments, the injection of the second aqueous cellular solution causes the release of the first interfacial film from the openings.

The wall with openings needs to be configured to establish the interfacial film with sufficient stability to maintain the integrity of a cellular layer in the respective channel long enough to create the emulated tissue structure. In some embodiments, the interfacial film can be formed from the injection of any of the aqueous solutions. In some embodiments, the wall is configured to establish the first interfacial film across the openings when injecting the first aqueous cellular solution. In some embodiments, the openings include a hydrophobic material to establish the first interfacial film across the openings of the first wall when injecting the first aqueous cellular solution. In some embodiments, the openings are outlined by opposing wedge-shaped edges that share a plane in order to establish the first interfacial film across the openings when injecting the first aqueous cellular solution. In some embodiments, the openings include a shape selected from the group consisting of circles and ovals. In some embodiments, the openings are outlined by polygonal-shaped structures, the structures providing opposing edges on at least two opposing sides of the opening, wherein the opposing edges share a plane in order to establish the first interfacial film across the openings of the first wall when injecting the first aqueous cellular solution. In some embodiments, the openings of the first wall are the spaces between adjacent columns along a series of columns; wherein, each column in the series of columns has a central axis that is at least substantially normal to the chip, each pair of adjacent columns provides a pair of opposing edges that share a plane in order to establish the first interfacial film across the openings of the first wall when injecting the first aqueous cellular solution.

In some embodiments, the systems can include three or more different cell types to emulate more complex tissue structures. In these embodiments, the systems further comprise a third channel; and, a third port configured for injection of a third aqueous cellular solution into the third channel. The systems include a second wall with openings, the second wall shared by the second channel and the third channel, and the openings in the second wall configured to (i) form a temporary, second aqueous interfacial film across the openings of the second wall upon the injection of the third aqueous cellular solution and (ii) allow for a cellular communication to occur between the second channel and the third channel upon a release of the interfacial film from the openings. In some embodiments, a multichannel microfluidics device can be used for the study of cellular interaction in blood vessels. For example, the device can be used to study the interaction between the 3 major arterial cells: endothelial, smooth muscle and adventitial cells.

The teachings herein show, for example, that we can emulate pulmonary arterial hypertension (PAH) in the development of a treatment for PAH. In some embodiments, the systems and methods taught herein can emulate PAH-induced right ventricular hypertrophy for the development of improved treatments. It should be appreciated by one of skill that these results prove that we can also emulate the communication between cells that result in pulmonary embolisms, and the environment of the embolisms themselves. And, as with the modeling of any of the human systems, we can look at the effects of any of several factors that may affect the efficacy of a therapy. For example, the systems and methods taught herein look at the relative effects of whether the subject is male or female, juvenile or adult, suffers another disease or physiological disorder, suffers a genetic disorder or is genetically predisposed to a condition, and the like. Any factor known to one of skill can be emulated using the systems and methods taught herein.

Using the systems and methods provided, one of skill can emulate any of a variety of cellular tissue interactions, and vascular tissue was used as a model herein. In some embodiments, the cellular interactions occur between vascular tissue layers. In some embodiments, the cellular interactions occur between vascular cell types. In some embodiments, the cellular interactions occur between vascular tissue layers. In some embodiments, the cellular interactions occur between vascular cells and a vascular extracellular matrix.

The develop of treatments can include the selection of a drug, the amount of the drug to administer, the tolerance of the drug, the stability of the drug, and the like. As such, the systems can be designed with separate injection ports and channels that can be used to feed the cells with growth media and administer a drug to test the response of the emulated tissue structure to the drug. And, since the cell culture medium may need to be replenished, in some embodiments, the system can further comprise a growth medium channel having a growth medium port.

The term "drug" can be used interchangeably with "active agent", "bioactive agent", and the like. The bioactive agents include, but are not limited to, small molecules, nucleotides, oligonucleotides, polynucleotides, amino acids, oligopeptides, polypeptides, and proteins. Bioactive agents can include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin 11, actinomycin X1, actinomycin C1, and dactinomycin (Cosmegen®, Merck & Co., Inc.). Antineoplastics or antimitotics include, for example, paclitaxel (TAXOL, Bristol-Myers Squibb Co.), docetaxel (TAXOTERE, Aventis S.A.), methotrexate, irinotecan, SN-38, azathioprine, vincristine, vinblastine, fluorouracil, doxorubicin hydrochloride (ADRIAMYCIN, Pfizer, Inc.) and mitomycin (MUTAMYCIN, Bristol-Myers Squibb Co.), and any prodrugs, codrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX, Biogen, Inc.), and any prodrugs, codrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINVIL and PRINZIDE, Merck & Co., Inc.); calcium channel blockers such as nifedipine; colchicines; fibroblast growth factor (FGF) antagonists, fish oil (omega 3-fatty acid); histamine antagonists; lovastatin (MEVACOR, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, codrugs, metabolites, analogs, homologues, congeners, derivatives, salts and combinations thereof. Antiallergic agents include, but are not limited to, pemirolast potassium (ALAMAST, Santen, Inc.), and any prodrugs, codrugs, metabolites, analogs, homologues, congeners, derivatives, salts and combinations thereof.

It should be appreciated from the teachings herein that treatments for PAH are provided, using the systems and methods taught herein. In some embodiments, drugs used for the treatment of PAH can include, but are not limited to epoprostenol, riociguat, bosentan, macitentan, ambrisentan, treprostinil, sildenafil, tadalafil, selexipag, and iloprost, and combinations thereof. Each of these drugs can be administered alone, or in combination, in some embodiments. In some embodiments, the drugs can be administered as follows in Table 1:

TABLE 1

| Drug | Dose |
|---|---|
| Epoprostenol | about 0.002 nmol/kg/min to about 0.030 nmol/kg/min by I.V.; in particular, 0.0028369 to 0.034043 by I.V. |
| Treprostinil | About 0.002 nmol/kg/min to about 003 nmol/kg/min by I.V.; in particular, 0.0016005 to 0.0032010 by I.V. nmol/kg/minute about 15.4 nmol to about 46.1 nmol by inhalation, one to nine inhalations taken four times daily; in particular, ranging from 15.365 nmol to 46.095 nmol each, four to nine inhalations daily |
| Iloprost | About 7.0 nmol to about 14.0 nmol by a single inhalation, six to nine inhalations daily, in particular, 6.9348 nmol to 13.870 nmol each inhalation, six to nine times daily |
| Selexipag | Oral administration 402.74 to 3221.9 nmol, each administration, twice daily |
| Bosentan | Oral administration, 113310 nmol to 226610 nmol each administration, two times daily |
| Ambrisentan | Oral administration, 13214 nmol to 26427 nmol, once daily |
| Macitentan | Oral administration, 8499 nmol to 16998 nmol, once daily |
| Riociguat | Oral administration, 1183.7 nmol to 5918.6 nmol each administration, three times daily; to find the proper dose for an individual, the amount can start at 1183.7 nmol each administration, three times daily, and can be gradually increased every two weeks in dose in increments of 1183.7 nmol per administration, three times per day, until a desired therapeutic response is seen, or until a dose-limiting toxicity occurs, up to a maximum dose of 5918.6 nmol, three times daily |
| Sildenafil | Oral administration, 8428.2 nmol to 42141 nmol each administration, three times daily I.V. administration, 10535 nmol to 21070 nmol daily; dose is adjusted for drug interactions when taking drugs in combination that affect efficacy of this drug |
| Tadalafil | Oral administration, 25680 nmol to 102720 nmol daily; dose is adjusted for drug interactions when taking drugs in combination that affect efficacy of this drug |

Of the above listed drugs, we have found that female PAH patients are more responsive to epoprostenol, treprostinil, selexipag, ambrisentan, bosentan and macitentan. As such, in some embodiments, methods of treating female PAH patients are provided. The methods can include, for example:

introducing a vascular endothelial cell tissue from a subject having PAH into a first channel of a microfluidics device taught herein, the introducing including seeding the vascular endothelial cell tissue into an aqueous cell growth medium to create an emulated vascular endothelial cell layer and injecting the emulated vascular endothelial cell layer into the first channel;

introducing a vascular adventitial cell tissue from the subject into a third channel of a microfluidics device taught herein, the third channel being separated from the first channel by a second channel, and the introducing including seeding the vascular adventitial cell tissue into an aqueous cell growth medium to create an emulated vascular adventitial cell layer and injecting the emulated vascular adventitial cell layer into the third channel;

introducing an aqueous cell growth media into the second channel to release (i) the interfacial film that separates the first channel from the second channel and (ii) the third channel from the second channel, the releasing of the interfacial films allowing communication between the emulated vascular endothelial tissue and the emulated vascular adventitial tissue;

identifying the best drug candidate for the subject by administering each of a plurality of drugs selected from the group consisting of epoprostenol, riociguat, bosentan, macitentan, ambrisentan, treprostinil, sildenafil, tadalafil, selexipag, and iloprost, and combinations thereof, to measure the therapeutic effect, including the activity, efficacy, dose response, stability, toxicity, and/or a combination thereof, to identify the best drug candidate or formulation for the subject; and, administering the best drug or formulation to the subject, if the therapeutic effect is desired.

In some embodiments, the method includes using a microfluidics device taught herein having at least 5 channels, wherein the emulated vascular endothelial tissue is injected into the second channel, the emulated vascular adventitial tissue is injected into the fourth channel, and cell growth media is injected into the first channel and the fifth channel, wherein the cell growth media can include one or more drug candidates to identify the best drug candidate or formulation. These methods can include forming a releasable interfacial film between the first channel and the second channel when introducing the emulated endothelial vascular tissue to the second channel, forming a releasable interfacial film between the fourth channel and the fifth channel when introducing the emulated endothelial vascular tissue to the fourth channel; and, releasing the interfacial films when injecting the cell growth media into the first and fifth channels, allowing for communication between the first channel and the second channel, and the fourth channel and the fifth channel. In some embodiments, the third channel is filled with an emulated vascular smooth muscle tissue layer, which can be in an aqueous-gel cell growth medium.

We have also found that male PAH patients are more responsive to sildenafil and tadalafil. In some embodiments, methods of treating male PAH patients are provided. The methods can include, for example:

introducing a vascular endothelial cell tissue from a subject having PAH into a first channel of a microfluidics device taught herein, the introducing including seeding the vascular endothelial cell tissue into an aqueous cell growth medium to create an emulated vascular endothelial cell layer and injecting the emulated vascular endothelial cell layer into the first channel;

introducing a vascular adventitial cell tissue from the subject into a third channel of a microfluidics device taught herein, the third channel being separated from the first channel by a second channel, and the introducing including seeding the vascular adventitial cell tissue into an aqueous cell growth medium to create an emulated vascular adventitial cell layer and injecting the emulated vascular adventitial cell layer into the third channel;

introducing an aqueous cell growth media into the second channel to release (i) the interfacial film that separates the first channel from the second channel and (ii) the third channel from the second channel, the releasing of the interfacial films allowing communication between the emulated vascular endothelial tissue and the emulated vascular adventitial tissue;

identifying the best drug candidate for the subject by administering each of a plurality of drugs selected from the group consisting of epoprostenol, riociguat, bosentan, macitentan, ambrisentan, treprostinil, sildenafil, tadalafil, selexipag, and iloprost, and combinations thereof, to measure the therapeutic effect, including the activity, efficacy, dose response, stability, toxicity, and/or a combination thereof, to identify the best drug candidate or formulation for the subject; and, administering the best drug or formulation to the subject, if the therapeutic effect is desired.

In some embodiments, the method includes using a microfluidics device taught herein having at least 5 channels, wherein the emulated vascular endothelial tissue is injected into the second channel, the emulated vascular adventitial tissue is injected into the fourth channel, and cell growth media is injected into the first channel and the fifth channel, wherein the cell growth media can include one or more drug candidates to identify the best drug candidate or formulation. These methods can include forming a releasable interfacial film between the first channel and the second channel when introducing the emulated endothelial vascular tissue to the second channel, forming a releasable interfacial film between the fourth channel and the fifth channel when introducing the emulated endothelial vascular tissue to the fourth channel; and, releasing the interfacial films when injecting the cell growth media into the first and fifth channels, allowing for communication between the first channel and the second channel, and the fourth channel and the fifth channel. In some embodiments, the third channel is filled with an emulated vascular smooth muscle tissue layer, which can be in an aqueous-gel cell growth medium.

The systems and methods provided herein work well to develop antibody treatments for subjects in need. Antibody therapy provides additional bioactive agents that may be useful when administered in combination with the methods taught herein. AVASTATIN, for example, is a human monoclonal antibody to VEGF, has provided beneficial results in colorectal cancer, increasing survival time by more than 30% when used in combination with the standard Saltz regime of irinotecan, 5-fluorouracil, and leucovorin. One of skill will appreciate that several monoclonal antibodies would be useful, the following providing further examples of the cancers that can be addressed using the systems and methods taught herein, and any of the bioactive agents taught herein, along with some monoclonal antibody therapies that may also be tested alone or in combination with any of the bioactive agents taught herein:

TABLE 2

| mAb name | Trade name | Cancer treated: |
|---|---|---|
| rituximab | RITUXAN | non-Hodgkin lymphoma |
| trastuzumab | HERCEPTIN | breast cancer |
| gemtuzumab ozogamicin* | MYLOTARG | acute myelogenous leukemia (AML) |
| alemtuzumab | CAMPATH | chronic lymphocytic leukemia (CLL) |
| ibritumomab tiuxetan* | ZEVALIN | non-Hodgkin lymphoma |
| tositumomab* | BEXXAR | non-Hodgkin lymphoma |
| cetuximab | ERBITUX | colorectal cancer; head & neck cancers |
| bevacizumab | AVASTIN | colorectal cancer; non-small cell lung cancer; breast cancer; glioblastoma; kidney cancer |
| panitumumab | VECTIBIX | colorectal cancer |
| ofatumumab | ARZERRA | chronic lymphocytic leukemia (CLL) |

*refers to a conjugated monoclonal antibody

Generally speaking, the cancers that can be addressed using the systems and methods taught herein include any known cancer. In addition, or including, the cancers in the list above, the following cancers are of interest: lung cancer, non-small cell lung cancer, adenocarcinoma, squamous cell carcinoma, large cell carcinoma, small cell lung cancer, bronchial cancer, colon cancer, rectal cancer, colorectal cancer, breast cancer, pancreatic cancer, prostate cancer, leukemia, acute myeloid leukemia, lymphoma, Hodgkins lymphoma, non-Hodgkin lymphoma, liver cancer, intrahepatic bile duct cancer, ovarian cancer, and esophageal cancer.

It should be appreciated that, a bioactive agent can be given alone or in combination with other bioactive agents, with the compositions and methods taught herein. Chemotherapy drugs, for example, are sometimes most effective when given in combination, as a combination chemotherapy regime. The rationale for combination chemotherapy is to use drugs that work by different mechanisms of action, thereby decreasing the likelihood that resistant cancer cells will develop. When drugs having different effects are combined, each drug can be used at its optimal dose, sometimes without, and sometimes reducing, intolerable side effects.

An active agent can be included, for example, in a pharmaceutically acceptable carrier, the active agent conjugated with the delivery system in an amount sufficient to exert a therapeutically useful effect in the absence of undesirable side effects on the patient treated. The therapeutically effective concentration may be determined empirically by testing the compounds in in vitro and in vivo systems described and then extrapolated therefrom for dosages for humans.

In some embodiments, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Likewise, pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In some embodiments, a therapeutically or prophylactically effective amount of a composition may range in concentration from about 0.001 nM to about 0.10 M; from about 0.001 nM to about 0.5 M; from about 0.01 nM to about 150 nM; from about 0.01 nM to about 500 µM; from about 0.01 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein in increments of 0.1 µM. In some embodiments, the compositions may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein in increments of 0.1 mg/kg.

Typically, a composition taught herein can be administered by subcutaneously, intramuscularly, intraperitoneally, or intravenously, injecting. A localized administration can, in some embodiments, include direct injection of an agent into the region of the tissue to be treated such as, for example, a solid tumor. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.0001% to about 10% (w/w), from about 0.01% to about 1%, from about 0.1% to about 0.8%, or any range therein, with the remainder comprising the excipient or excipients.

In some embodiments, the composition can be administered in conjunction with at least one other therapeutic agent for the disease state being treated, especially another agent capable of treating cancer such as, for example, a chemotherapeutic agent. The amounts of the agents needed can be reduced, even substantially, such that the amount of the agent or agents required is reduced to the extent that a significant response is observed from the subject. A significant response can include, but is not limited to, a reduction or elimination of nausea, a visible increase in tolerance, a faster response to the treatment, a more selective response to the treatment, or a combination thereof.

The methods can further comprise the administration of an effective amount of an antiproliferative, an effective amount of radiation therapy, surgical therapy, or a combination thereof. The teachings are also directed to a method of treating a cancer. In some embodiments, the method comprises administering an agent to a subject in need of a cancer treatment, wherein the dose of the agent is selected to reduce or eliminate an immunosuppression that would otherwise occur when administering a substantially higher dose of the agent in the subject; and administering radiation therapy in combination with the agent, wherein the reduction or elimination of the immunosuppression enhances the efficacy of the radiation therapy when compared to the efficacy of the radiation therapy otherwise observed when administered in combination with the substantially higher dose of the agent in the subject. In some embodiments, the agent comprises one or more chemotherapeutic agents in combination with the agents provided herein. In these embodiments, the agent can be selected from the group consisting of dacarbazine, paclitaxel, doxorubicin, or a combination thereof.

In some embodiments, an effective amount can range, for example, from about 1 mg/day to about 1000 mg/day, from about 10 mg/day to about 500 mg/day, from about 50 mg/day to about 250 mg/day, or any range or amount therein in increments of 1 mg/day, for a human of average body mass.

In some embodiments, an average human body mass can be estimated at 60 kg, 65 kg, 70 kg, 75 kg, 80 kg, or any mass therein in increments of 1 kg. For treating a solid tumor, a similar amount will be therapeutically effective. A person of ordinary skill in the art will be able without undue experimentation, having regard to that skill and this disclosure, to determine a therapeutically effective amount of the compositions of this invention for a given disease.

In some embodiments, G-CSF is administered in combination with a composition taught herein using any amount, time, and method of administration known to be effective by one of skill. The G-CSF can be NEUPOGEN, for example, administered in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range or amount therein in increments of 1 µg/kg.

In some embodiments, the radiation therapy can be administered in a single, localized high-dose ranging, for example, from about 20 Gy to about 100 Gy. In some embodiments, the radiation therapy can be administered in a total dose ranging from about 20 Gy to about 100 Gy using a modified hypofractionation regime of dosing comprising from about 2 doses to about 5 doses during a time frame of one week. In some embodiments, the radiation therapy can be administered in a total dose ranging from about 20 Gy to about 100 Gy using a modified hypofractionation regime of dosing comprising from 2 doses to 3 doses during a time frame ranging from about 2 days to about 3 days. The radiation therapy can also be administered in a total dose ranging from about 45 Gy to about 60 Gy using a modified hypofractionation regime of dosing comprising administering a single dose ranging from about 15 Gy to about 20 Gy for each day during a 3-day time frame.

The compositions and therapies taught herein can be administered in combination. For example, the combinations can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Likewise, the systems can be designed for multiple growth medium ports, each for supplying cell media to feed the cells and a select drug to test. As such, in some embodiments, the systems can further comprise a first growth medium channel having a first growth medium port and located in communication with the first channel and a second growth medium channel having a second growth medium port and located in communication with the second channel.

In the development of treatments, the systems can be designed to emulate diseased tissue or a disease process. As such, in some embodiments, a method of emulating a disease in a subject is provided. The methods can comprise obtaining one of the systems taught herein; injecting the first aqueous cellular solution into the first channel to introduce a first cell of the disease, the injecting forming the temporary, first aqueous interfacial film across the openings of the first wall; and, injecting the second aqueous cellular solution into the second channel to introduce a second cell of the disease. In these embodiments, the first interfacial film releases after the injecting of the second aqueous solution; and, the first cell and the second cell communicate after the releasing of the first interfacial film to emulate the disease state.

In some embodiments, the system chosen has at least three channels, and at least three different cell types in the emulated tissue structure. As such, in some embodiments, the method of emulating a disease comprises obtaining a microfluidics system taught herein, the system having at least three channels; injecting the first aqueous cellular solution into the first channel to introduce a first cell of the disease, the injecting forming the temporary, first aqueous interfacial film across the openings of the first wall; injecting the third aqueous cellular solution into the third channel to introduce a third cell of the disease, the injecting forming the temporary, second aqueous interfacial film across the openings of the second wall; and, injecting the second aqueous cellular solution into the second channel to introduce a second cell of the disease. In these embodiments, the first interfacial film releases after the injecting of the second aqueous solution; the second interfacial film releases after the injecting of the second aqueous solution; the first cell and the second cell communicate after the releasing of the first interfacial film to emulate the disease state; and, the second cell and the third cell communicate after the releasing of the second interfacial film to emulate the disease state.

An aqueous gel cell growth medium can be used in some embodiments. The gel can be used in an alternating channel to further stabilize the integrity of at least three channels and slow the speed at which the tissues interact. As such, in some embodiments, the method of emulating a disease in a subject can comprise obtaining a system having at least three channels; injecting the first aqueous cellular solution into the first channel to introduce a first cell of the disease, the injecting forming the temporary, first aqueous interfacial film across the openings of the first wall; injecting the third aqueous cellular solution into the third channel to introduce a third cell of the disease, the injecting forming the temporary, second aqueous interfacial film across the openings of the second wall; and, injecting the second aqueous cellular solution into the second channel in the form of an aqueous gel to introduce a second cell of the disease. The first interfacial film can release after the injecting of the second aqueous solution; the second interfacial film can release after the injecting of the second aqueous solution; the first cell and the second cell communicate after the releasing of the first interfacial film to emulate the disease state; and, the second cell and the third cell communicate after the releasing of the second interfacial film to emulate the disease state.

The methods of emulating a tissue structure, and emulating a disease, lead naturally to methods of treating the diseased tissue structure. As such, method of treating an emulated disease with a drug are provided. In some embodiments, the methods can include performing a method of emulating disease as taught herein; selecting a drug to treat the emulated disease; and, administering the drug in any one of the channels. In some embodiments, the drug can be administered in any channel. In some embodiments, the drug can be administered in the first channel or the second channel. In some embodiments, the drug can be administered in the first channel, the second channel, or the third channel. In some embodiments, the drug can be administered in the first channel, the second channel, the third channel, the fourth channel, or the fifth channel. In some embodiments, the drug can be administered in the first channel or the third channel. In some embodiments, the drug can be administered in the first channel or the fifth channel.

Various types of diseases can be emulated and treated using the systems and methods provided herein. In some embodiments, the methods are directed to treating an emulated vascular disease with a drug. In these embodiments, the methods can include obtaining a system taught herein, the system having at least three channels for the introduction of three vascular cell types; injecting the first aqueous cellular solution into the first channel to introduce a first cell of the disease to form an adventitial cell layer, the injecting forming the temporary, first aqueous interfacial film across the openings of the first wall; injecting the third aqueous cellular solution into the third channel to introduce a third cell of the disease to form an endothelial cell layer, the injecting forming the temporary, second aqueous interfacial film across the openings of the second wall; and, injecting the second aqueous cellular solution into the second channel to introduce a second cell of the disease to form a smooth muscle layer. These methods further comprise selecting a drug; and, administering the drug to the first growth medium channel or the second growth medium channel. In these embodiments, the first interfacial film releases after the injecting of the second aqueous solution; the second interfacial film releases after the injecting of the second aqueous solution; the first cell and the second cell communicate after the releasing of the first interfacial film to emulate the disease state; and, the second cell and the third cell communicate after the releasing of the second interfacial film to emulate the disease state.

Example 1. Pillar Shape

The integrity and stability of an interfacial film includes consideration of surface tension and contact angle. The surface tension is provided by the composition of the pillar and the composition of the aqueous material used to form the film, for example, a cell growth media.

Figures 4A, 4B, 4C:
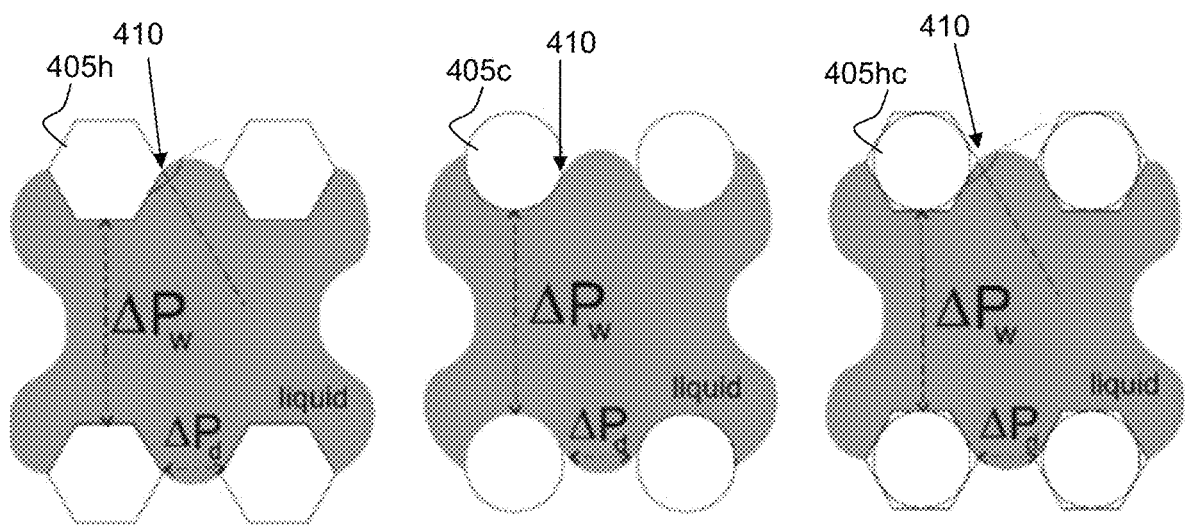
FIGS. 4A-4C illustrate the difference in contact angle between the interfacial film and the pillars, comparing round pillars to hexagonal pillars, according to some embodiments.

FIGS. 4A-4C illustrate the difference in contact angle between the interfacial film and the pillars, comparing round pillars to hexagonal pillars, according to some embodiments. The pillars were fabricated from polydimethylsiloxane (PDMS) casting, and a glass coverslip was added to the device using ambient plasma treatment for 2 minutes (PDC-001-HP series, Harrick plasma, NY) at medium RF power. The device was then stored in an oven at 80° C. for 2 hours to enhance bonding. The chips were then treated with UV (UV Light Box Benchtop Decontamination Chambers, Air science Inc.) for 45 minutes to sterilize before proceeding to cell seeding steps. The pillars were then coated with poly-D-Lysine (PDL) solution (2 mg/ml) to enhance adhesion to the pillars. Chips can also be fabricated with a wide variety of thermoplastic polymers such as oly(methyl methacrylate) (PMMA), polycarbonate (PC), polystyrene (PS), polyvinyl chloride (PVC), polyimide (PI), cyclic olefin copolymer (COC), cyclic olefin polymer (COP), and cyclic block copolymer (CBC). The chips prepared with these polymers can attached with cover slips made of the same polymers.

Cell media was then introduced into the channel, and the contact angle was measured. FIG. 4A shows the contact angle between the interfacial film and a hexagonal pillar. FIG. 4B shows the contact angle between the interfacial film and a circular pillar. FIG. 4C shows an overlay of the hexagonal pillar with the circular pillar to illustrate the contact angle differences. FIGS. 4A-4C illustrate that there is a difference in pressure across the channel $\Delta Pw$ and the pressure between the pillars $\Delta P$. Pillars having round, hexagonal, and trapezoidal shapes were compared.

Example 2. Interpillar Distance

The surface tension and contact angle can be optimized to strengthen the integrity and stability of the interfacial film, and the distance over which the film is stretched is also a factor to consider.

Figure 5:
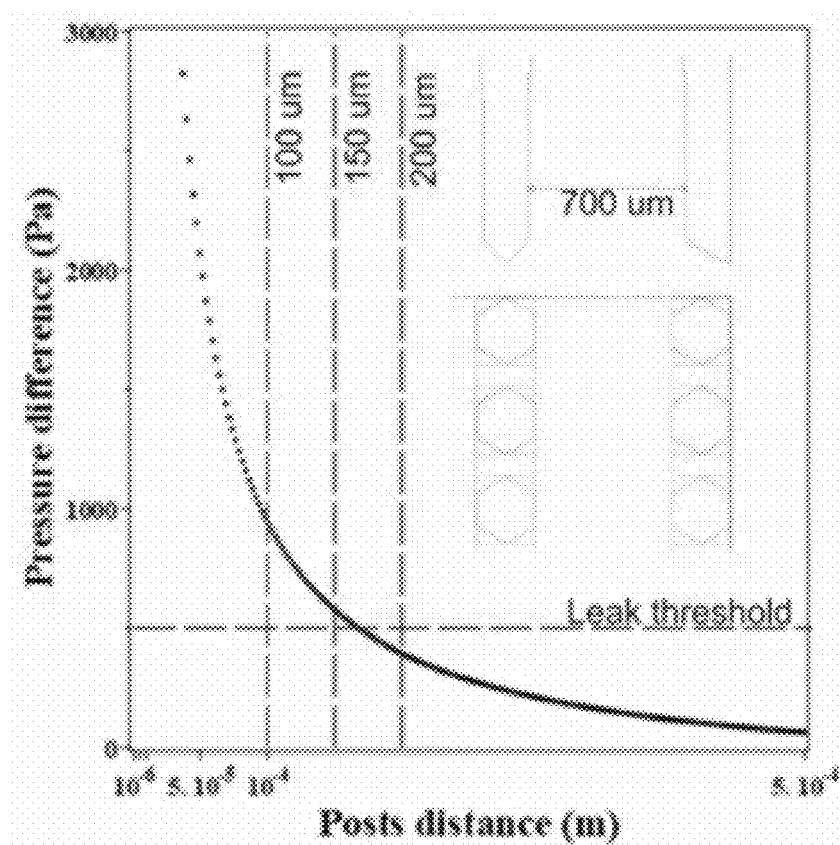
FIG. 5 is a graph shown that there is a preferred interpillar distance between hexagonal pillars that avoids leakage of the interfacial film, according to some embodiments.

FIG. 5 is a graph shown that there is a preferred interpillar distance between hexagonal pillars that avoids leakage of the interfacial film, according to some embodiments. It can be seen that, with the hexagonal pillars, the leak threshold was over 150 uM, meaning that the pillars could span up to at least 150 uM and maintain a stable interfacial film with no leakage.

Leaks began occurring as the interpillar distance approached 200 uM, as shown by the line crossing the leak threshold in FIG. 5. All pillars, whether having round, hexagonal, and trapezoidal shapes did not leak below an interpillar distance of 100 uM.

Example 3. Creating a 5-Channel, Multichannel Microfluidics Device

A microfluidics chip can be prepared, for example, having 5 main channels, and micropillars for a three-dimensional (3D) environment as follows:

For fabrication of this device, a network of 5 channels was created, each channel being 1 mm wide and 3 cm long. AutoCAD was used in the process. The channels were separated by 150 m tall trapezoidal pillars, placed 200 m apart throughout the length of the channel.

From a CAD file, we created a photomask, printed the mask in a high-resolution printer (CAD Art Services Inc., OR), and then placed the mask on a silicon wafer, spin coated (Spin Coater WS-650 Series, Laurell Technologies Corporation, PA) using SU-8-photoresist polymer (Micro-Chem Inc., MA), and baked at 65° C. for 5 min and 95° C. for 25 min. We then exposed the SU-8-coated silicon wafer to UV light (UV-KUB 2, KLOE Inc., France), baked again at 65° C. for 5 min and 95° C. for 12 min, cooled it to room temperature, and washed it with SU-8 solvent to obtain a silicon master mold. To fabricate the devices using the master mold, we poured an aliquot of polydimethylsiloxane (PDMS, Dow Inc., MI) mixed with a curing solution (Dow Inc., MI), with a ratio of 10:1, over the mold. We then degassed, baked, and cut out the individual devices (35 mm diameter, 3-4 mm height), and finally created inlets and outlets using a biopsy Punch® (Miltex, PA).

Making the microfluidics chip: polydimethylsiloxane (PDMS)-based chips with micropillars can be used for lab scale experiments. However, cyclic-olefin-copolymer (COC) and injection molding can be used to produce a large number of chips for a large scale use. Pillars were used to create the wall with openings. In this embodiment, due to the desire to have opposing edges to obtain the surface tension that holds the interfacial film, rounded features were not used on the pillars. This is an example of an embodiment in which round or spherical "pillars" were not used.

Operating the chip: obtain a pumping system that can be implemented to automate pumping rather than use manual pipettes. See, for example, https://www.sciencedirect.com/science/article/pii/S2468067220300249?via%3Dihub (downloaded Jul. 27, 2021; teaches a peristaltic pump suitable for this application); see also, for example, https://link.springer.com/article/10.1140/epje/s10189-020-00002-9 (downloaded Jul. 27, 2021; teaches a constant pressure pump suitable for this application).

Manual Seeding, Growth, and Evaluation

A pathological condition can be established using manual seeding of the cells, growing of the manually placed cells using manual processes, establishing and releasing an interfacial layer to allow for cellular interactions.

Automation of the Device

We can automate the process for cell seeding and growing in a sterile environment. The automated device will be easier to use and can be used at the patient bedside, for example, to evaluate therapeutic response, investigate the effects of sex and age on the therapeutic response, as well as any of a multitude of other factors known to those of skill, to develop a personalized approach to the therapy of the subject.

Example 4. Studying Pulmonary Arterial Hypertension Applications

Pulmonary arterial hypertension (PAH) is a rare disease in which pulmonary arteries/arterioles become stiffer and occluded. The heart must work harder to pump blood through the occluded arteries into the lungs. In so doing, the heart becomes enlarged, and patients die of right heart failure. The chief clinical manifestation of the disease is elevated mean pulmonary arterial pressure (mPAP) that results from an array of active structural alterations in the pulmonary artery, called arterial remodeling and muscularization. The chief cause of death in patients with pulmonary arterial PAH, for example, is right ventricular hypertrophy (PAH-RVH). The various cellular and bio-molecular processes that are implicated in the genesis of PAH-RVH are poorly understood and can be better treated using the systems and methods taught herein.

This pathology develops because of an aberrant proliferation, migration, and misplaced growth of pulmonary arterial cells (PACs), development of apoptosis resistant endothelial cells (ECs), enhanced deposition of extracellular matrices (ECMs), thickening of smooth muscle layers, and acquisition of smooth muscle cell (SMCs) like phenotypes by ECs. Due to the chaotic cellular growth, the disease becomes severe and some pulmonary arteries develop glomeruloid-like luminal occlusions called plexiform lesions. These lesions are described as a plexus of slit-like channels lined with endothelial cells separated by hyperchromatic and oval core cells of uncertain phenotype.

Influence of Gender on PAH

One of the puzzling aspects of PAH is that it affects more women than men but women with PAH tend to live longer than men. This disparity in the prevalence versus survival of PAH patients is believed to have resulted from intrinsic differences between the two sexes and the conflicting roles of sex hormones, especially estrogen, which appear to have both beneficial and detrimental effects in the genesis and progression of PAH in females. Further, we've found that human and animal studies suggest that the sex of the subjects plays a role in therapeutic response for PAH and thus a sex-based personalized therapy would presumably benefit PAH patients.

Investigating ECM Remodeling

As reported in our recent publication, we first characterized the cells for various markers and seeded control and PAH cells on the respective channels of the chips at a density of $2 \times 10^6$ cells/mL of adventitial cells (ADCs) or SMCs and $5 \sim 10 \times 10^6$ cells/mL of ECs. SMCs were seeded in rat tail type I collagen solution (Corning Inc., NY). We fed the cells with the media via the two outermost channels. In experiment when chips were seeded with three different cell types, we first instilled collagen (2 mg/mL) alone or SMC mixed with collagen into the medial channel and allowed 20 minutes for collagen to form gel and then seeded ECs and ADCs 20 minutes apart. The cell-laden chips thus prepared were placed in a humidified chamber and let them grow in a $CO_2$ incubator for 5-8 days. Each day, the medium was removed and replaced with 150 μL fresh media.

On day 1, 3, 5, 7, and 10, we stained ECs, SMCs, and ADCs with markers for CD31, FSP-1, VEGFR2, α-SMA, SM-22α, CD90 and for markers of various ECM proteins. For staining the cells, we first washed the chips with the basal media, treated with 4% paraformaldehyde, blocking buffer, primary antibodies and incubated overnight. On the following day, we again washed the chips with washing buffer, instilled secondary antibodies, incubated for an hour, washed again, and finally treated with the mounting medium with DAPI to stain the nuclei. Similarly, we stained the chips to determine the presence of human collagen type I (ColT1) and IV (ColT4), laminin, tenascin-C, fibronectin, elastin. We took images of cells and ECMs using an epifluorescence (DMi8 epifluorescence, Leica, IL) or a multi-photon confocal microscope (Ti-E, Nikon, NY).

We quantitated various ECMs using a quantitative PCR (qPCR) method. For this, we removed and collected both control and PAH cells after 1, 3, 5, 7, and 10 days of seeding. Using a Quick Prep Micro mRNA purification kit (Amersham, Piscataway), we isolated mRNA and analyzed for laminin, tenascin-C, ColT1α, ColT4, fibronectin and elastin. Based on manufacturer's protocol, we generated single-stranded cDNA using the Superscript III first strand synthesis system (Invitrogen) and performed qPCR in an MX4000 using Brilliant SYBR Green QPCR Master Mix at threshold cycle numbers generated by MX4000 software v. 4.20 (Stratagene, La Jolla, CA). Using the equation $\Delta Ct=Ct$ reference gene-Ct gene of interest, we normalized Ct values to internal control GAPDH.

Evaluation of Endothelial Cell Dysfunction on the Chips

For investigating whether endothelial cells undergo apoptosis like that observed in PAH, we seeded control endothelial cells, smooth muscle cells and ADCs and grew the cells at various conditions such as regular serum in normoxia or reduced serum at hypoxia for 3 to 5 days. We also grew N-ECs in the presence or absence of collagen. At the end of the experiment, we stained the cells for the same cellular and ECM markers as listed above. For evaluating apoptosis, we stained the cells for the presence of λ-H2AX, PCNA and cleaved caspase-3 and finally calculated apoptotic index from the ratio of the number of caspase-3 positive cells to the total number of cells.

Assessing Sex-Specific Therapeutic Response:

For assessing the cellular basis of these sex-specific therapeutic effects, we used bosentan, an endothelin receptor antagonist (ERA), to which female PAH patients are more responsive than male patients. Into chips prepared by seeding PAH-ECs/SMCs/ADCs of male and female patients, we infused 50 µM bosentan starting from day 4 of cell seeding and continued the infusion for an additional 3 days. To determine whether the drug had any preventive effects, we treated the cell-laden chips with 50 µM bosentan on day 1 of seeding and let the cells grow for 6 more days with no treatment. For studying the influence of growth hormones and anti-PAH drug on cellular functions and remodeling, we seeded male and female PAH-ECs, QD705-labeled or unlabeled PAH-SMCs and PAH-ADCs. We assessed the deposition of human ColT1, expression of aromatase (an enzyme that synthesizes estrogen) and CYP1B1 (an estrogen-metabolizing enzyme) and then measured arterial remodeling and muscularization.

For assessing the effect of the drug pulmonary arterial thickening, we assumed that ECs and SMCs grow in their respective channels, the intimal and medial layers of the chip, not outside their assigned layers. If ECs or SMCs grow outside their original seeding channels, we considered out-of-designated channel growth as intimal or medial layer thickening, respectively. We also considered the migration of SMCs from the medial to intimal as muscularization and that the number of SMCs that grow in the intimal layers is the degree of muscularization. These assumptions were based on PAH pathology whereby non-muscularized distal arteries/arterioles become muscularized and show SM-like cells from preexisting SMCs. We used phase contrast microscopy, immunostaining, and quantum dot labeling to draw line between the growth zones of different cells and for counting and identifying cells.

For demarcating boundaries of different cell growth areas, we first imaged the chips using a phase-contrast microscope and then stained the cells for imaging using a confocal microscope. For calculating the extent of intimal and medial thickening, we calculated the average of the lengths of five to seven diametrically uneven points of the same layer. To determine the degree of muscularization, we grew QD-labeled N-SMC/PAH-SMCs on the chip and stained the chips for FSP-1 and CD31 antibodies and counted the number of FSP-1+CD31– or QD-labeled SMCs in all three layers of the chip.

Creation of On-Chip Plexiform-Like Complex Cellular Lesions

To recapitulate plexiform lesions on the chips, we first prepared spheroids or 3D colonies of various combinations of cells, using the "hanging drop method". See, for example, R. Foty. J Vis Exp. 51:2720(2011). The spheroids were then seeded on the chips. In short, by dispersing ~5×105 ECs, EC/SMC (1:1), EC/ADC (1:1) or EC/SMC/ADC (1:1:1) in 25 mL of a serum-free medium containing 20% methyl cellulose, we prepared a mixture of cells in methyl cellulose. Then, using a pipette, we aliquoted the cell-methyl cellulose mixture into 25-µL droplets and seeded a series of 25-µL droplets onto non-adherent cell culture dishes. We then inverted the dishes containing cell droplets so that the droplets remained suspended from the dish surfaces in the air and thus created hanging-cell droplets. By incubating the cell droplets, suspended in the air, for 24 hrs at 37° C. and 5% $CO_2$, we created spheroids or 3D colonies of single and multiple cells. We prepared spheroids of QD-labeled PAH-ECs, PAH-EC/SMCs, or PAH-EC/SMC/ADCs and spheroids of control cells (N-EC/SMC/ADCs). The next day, after collecting the spheroids, we washed them with the medium to remove methyl cellulose and then dispersed them in 90 µL of collagen as a spheroid matrix. Finally, we seeded 10-15 spheroids on the intimal channels of the chips. Three days after seeding of the spheroids onto the chips, we treated the chips containing control N-EC/SMC/ADC spheroids with 50 ng/mL VEGF and 1 ng/mL TGF-β for an additional 3 days. We then stained the ECs, SMCs, and ADCs with various markers and examined the cells under a confocal microscope (Ti-E, Nikon, NY).

Results

By growing three pulmonary arterial cells (PACs), namely endothelial cells (ECs), smooth muscle cells (SMCs), and adventitial cells (ADCs), the PAH pathophysiology on the device is recreated. The PAH cells can be obtained, for example, from biopsies or using PACs differentiated from PAH patient-derived induced pluripotent stem cells.

Diseased (PAH) PACs, when grown on the chips, moved of out their designated layers, interacted with the cells in the neighboring layers, and created phenomena similar to the major pathologies of human PAH: muscularization, deposition of extracellular matrix (ECM) proteins, and arterial remodeling. The results included the following:
  Flow-induced stress caused control cells, grown on the chips, to undergo morphological changes and elicit arterial remodeling.
  Estrogen and platelet-derived growth factor (PDGF) treatment caused more extensive arterial remodeling in chips prepared with PACs of female patients than in chips with PACs of male patients.

Female chips (chips prepared with cells from female patients) were more responsive to bosentan, an anti-PAH drug, than male (chips prepared with cells from male patients) chips.

Spheroids of PAH-EC/SMC/ADCs, but not of control cells, seeded on the chips evolved into arteries with plexogenic-like lesions, where PAH-ECs showed a clonal proliferative nature.

Figure 6:
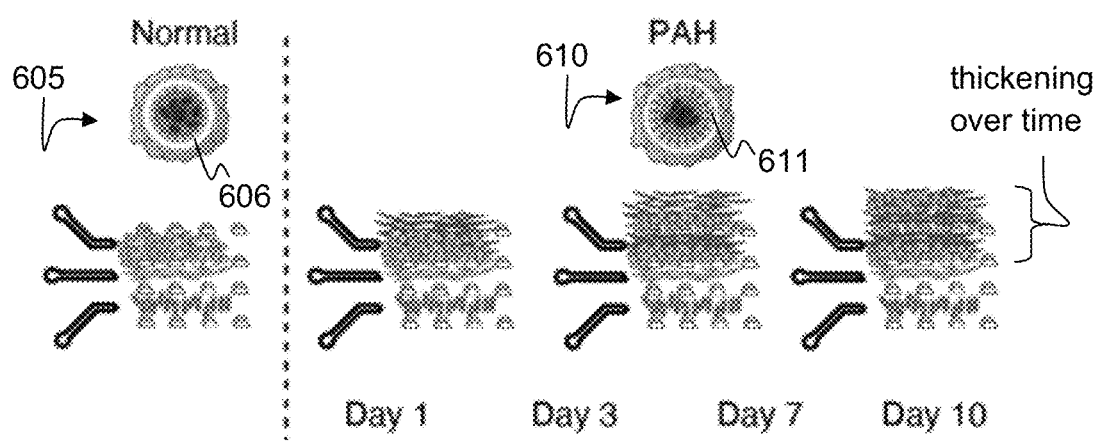
FIG. 6 illustrates extracellular remodeling in PAH, according to some embodiments.

FIG. 6 illustrates extracellular remodeling in PAH, according to some embodiments. The systems and methods provided herein created a PAH representation that showed ECM remodeling like that of pulmonary arteries of clinical patients.

Since the deposition of ECM is a major pathological feature of PAH, the systems and methods were used to show that PAH cells grown on chips produce ECM proteins, create their own ECM scaffolds and thus cause pulmonary arterial remodeling. The basement membrane of a normal human pulmonary artery 605 consists of a thin sheet of fibers underlying the endothelial cell layer, formed by specific interactions between ECM components, such as laminins, collagens, elastin, fibronectin, tenascin C, and proteoglycan. Thus, we measured the levels of ECM proteins in the chips prepared with 3 types of control and PAH cells. Compared with the control chips, the chips prepared with PAH cells showed extensive deposition of various ECM proteins: laminin, tenascin-C, and insoluble collagen (ColT1α), but not ColT4, fibronectin or elastin. In chips prepared with PAH cells, a thin layer of laminin was developed and propagated toward both the intimal and the luminal compartments; intimal thickening increased with the increase in the laminin deposition. In the intimal layer of PAH chips, there were fibril-like collagen fibers that increased 611 with the increasing of number of PAH-SMCs in the intimal layers. The deposition of collagen fibers was the highest in the intimal layers of the PAH chips. A compartment-specific analysis of the pulmonary arteries of IPAH patients revealed that alteration in ECM remodeling, specifically collagen expression, was more pronounced in the intimal followed by medial and then in the adventitial layers.

We also studied the effect of sex on the development of plexiform lesions by seeding spheroids of various combinations of PAH cells from male and female patients (PAH-ECs/SMCs, PAH-ECs/ADCs, and PAH-ECs/SMCs/ADCs). For ease of identification, we used QD705-labeled PAH-ADCs and N-ADCs. Male and female PAH-EC spheroids gave rise to angiogenesis-like sprouting, with a luminal arterial channel lined by a single layer of ECs, but no lesions. Male and female PAH-EC/SMC spheroids similarly developed into arteries without lesions. In contrast, PAH-EC/ADC spheroids formed disorganized masses with an arterial lumen, but a few cuboidal-like vessels were observed only in female plexiform-mimicking chips. In both sexes, spheroids of PAH-ECs/SMCs/ADCs gave rise to plexiform-like complex cellular lesions. Female chips showed more upregulation of α-SMA than male chips, and female PAH-SMCs contained intermediary filaments, suggesting that SMCs are in the differentiating stage.

Example 5. Developing Treatments for Disease

The systems and devices presented herein are useful in developing treatments for disease as they can emulate the salient pathophysiological features of disease processes, as well as the cellular interactions and response to drug administration. In the case of PAH, the cell types are the three major cell types of the pulmonary artery. The interactions include, for example, the migration of cells from one layer of pulmonary artery wall to another, endothelial to mesenchymal transition, and the formation of plexiform-like lesions. In the case of PAH, we have shown the differences and similarities in the pathogenesis of PAH in male and female patients and use these differences and similarities to develop sex and age specific therapy for PAH. This process can help in developing personalized therapies for disease processes. See, for example, Taslim A. Al-Hilal, et al. Royal Society of Chemistry, Lab Chip 20: 3334-3345 (2020), https://doi.org/10.1039/D0LC00605J (downloaded Jul. 27, 2021), which is hereby incorporated herein by reference in it's entirety.

We studied the effect of sex on the development of plexiform lesions by seeding spheroids of various combinations of PAH cells from male and female patients (PAH-ECs/SMCs, PAH-ECs/ADCs, and PAH-ECs/SMCs/ADCs). For ease of identification, we used QD705-labeled PAH-ADCs and N-ADCs. Male and female PAH-EC spheroids gave rise to angiogenesis-like sprouting, with a luminal arterial channel lined by a single layer of ECs, but no lesions. Male and female PAH-EC/SMC spheroids similarly developed into arteries without lesions. In contrast, PAH-EC/ADC spheroids formed disorganized masses with an arterial lumen, but a few cuboidal-like vessels were observed only in female plexiform-mimicking chips. In both sexes, spheroids of PAH-ECs/SMCs/ADCs gave rise to plexiform-like complex cellular lesions. Female chips showed more upregulation of α-SMA than male chips, and female PAH-SMCs contained intermediary filaments, suggesting that SMCs are in the differentiating stage.

The sex-disparity in PAH and the sex-preferential response to PAH therapy are two perplexing features of PAH pathophysiology. Although PAH affects more females than males, the survival rate in males is worse than in females. Major factors that contribute to sex-disparity in PAH include sex hormones and growth factors. Some reports suggest differences in cell cycle regulation of PACs predispose women to PAH. Further, both human and animal studies suggest that sex of the subjects plays a role in therapeutic response for PAH and thus a sex-based personalized therapy may presumably benefit PAH patients.

Example 6. Developing Treatments

As taught herein, the systems and methods can be used to emulate cellular interactions in any system of the body in the development of treatments for disease. In some embodiments, the systems and methods provided herein can emulate any vascular disease.

Pulmonary vascular diseases include far more than PAH, and such diseases include several pathological conditions that alter the blood vessels serving as a conduit between heart and the lungs. With regard to the scope of pulmonary vascular diseases that can be investigated using the systems and methods herein, any diseases having alternations in the pulmonary vasculature, such as stiffening pulmonary vascular bed, for example, can cause various complications that can be addressed in the development of improved treatments.

Figure 7:
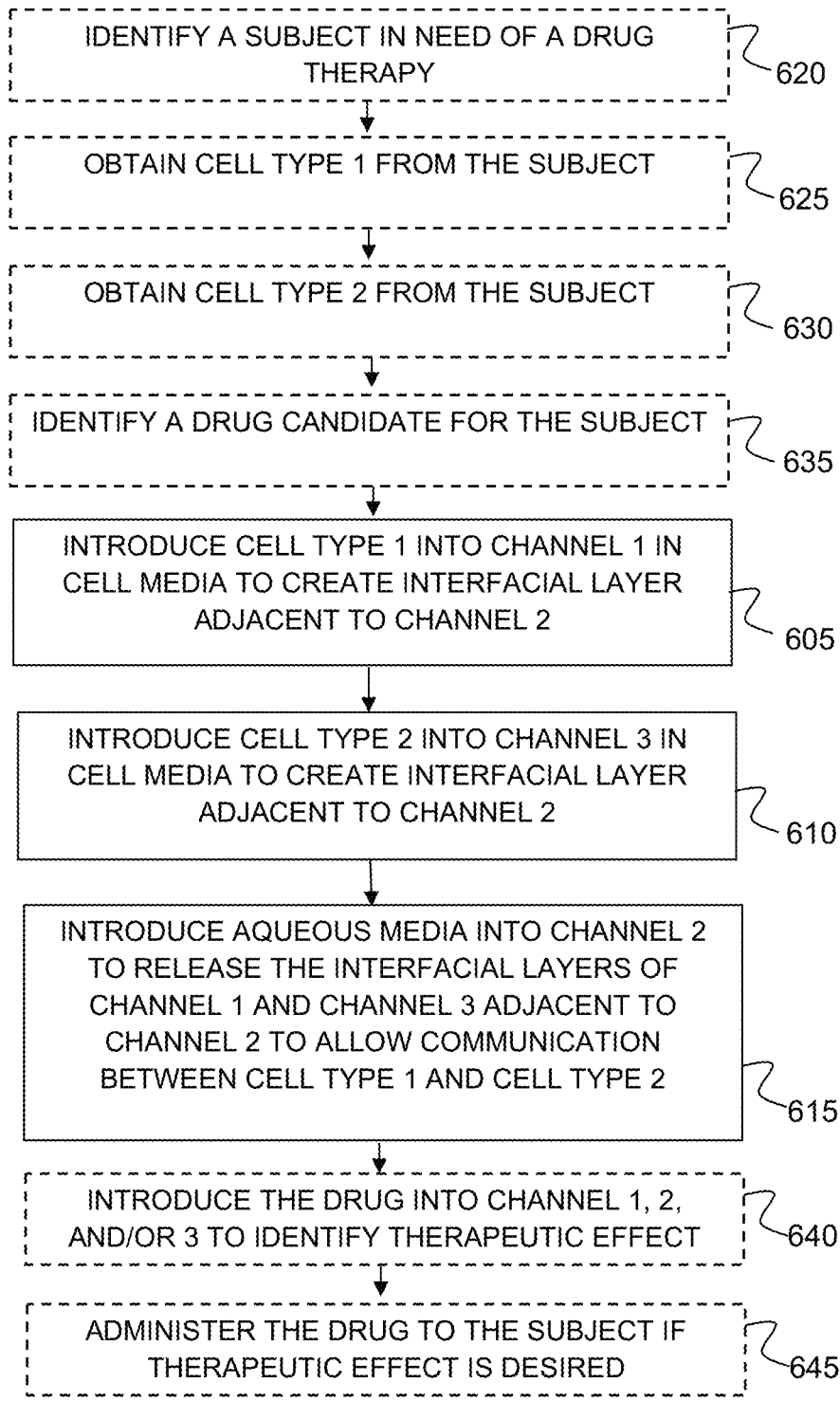
FIG. 7 illustrates a flowchart of how the systems and methods taught herein can be used to treat a subject in need, according to some embodiments.

FIG. 7 illustrates a flowchart of how the systems and methods taught herein can be used to treat a subject in need, according to some embodiments. In many of the systems taught herein, the microfluidics device will have at least 3 channels. Steps 605, 610, and 615 introduce a first cell type, cell type 1, into channel 1 in a cell media to create an interfacial layer adjacent to channel 2; introduce a second cell type, cell type 2, into channel 3 in a cell media to create an interfacial layer adjacent to channel 3; and, introduce an aqueous media into channel 2 to controllably release the interfacial layers adjacent to channel 2, allowing the communication between cell type 1 and cell type 3 to occur. These are the core steps. Steps 620, 625, 630, 635, 640, and 645 take the systems and methods to identifying 620 a subject in need of a drug therapy, obtaining 625 a cell type 1 from the subject, obtaining 630 a cell type 2 from the subject, identifying 635 a drug candidate for the subject, introducing 640 the drug into channel 1, 2, and/or 3 to identify therapeutic effect, and administering 645 the drug to the subject if the therapeutic effect is desired.

For a vascular model you can have three cell types: smooth, adventitial, and endothelial cells. In some embodiments, a 3 channel device, the smooth cell can be placed in the middle channel, channel 2, and the adventitial and endothelial cells can be placed in adjacent channels 1 and 3. In some embodiments, a 5 channel device, channels 1 and 5 can act as cell media reservoirs, which can be periodically changed as needed, and can also be used to administer drug; channels 2 and 4 can be adventitial and endothelial cells; and channel 3 can be smooth muscle cells. The smooth muscle cells can be introduced in a aqueous gel, cell media or an aqueous fluid, cell media. In some embodiments, channel 1 and/or channel 5 can be used to apply hydrostatic pressure to emulate blood pressure changes, simulating stress on the vessels, placing the endothelial cell layer adjacent to one or both channels 1 and 5. Given that capillaries have only endothelial cells, and major arteries have all three layers, one of skill will appreciate how the systems and methods can be used to represent the physiology in the development of treatments.

Sex-specific therapies: Our studies have suggested that chips prepared with PACs from female PAH patients are more responsive to estrogen treatment than the chips prepared with PACs from male PAH patients. Here, we employed the chips for studying sex-specific therapeutic responses by treating the chips with bosentan, an endothelin receptor antagonist. True to the clinical data, which showed female PAH patients were responsive to bosentan therapy than male patients (p=0.3), chips prepared with PACs from female patients were more responsive to bosentan than male counterparts. In female chips, the drug reduced the thickening of the medial layer, slowed the migration of PAH-SMCs toward the luminal and intimal layers, and lowered CYP1B1 expression in the medial layer. Compartment-specific analysis showed that laminin and ColT1α deposition were lower in bosentan-treated female chips than in the male chips. For studying the preventive effect, we treated male and female chips on day one after seeding and then let the cells to grow for another 6 days without treatment. Although the extent of thickening of intimal and medial layers were similar in male versus female chips, the presence of PAH-SMCs in the endothelial layer was lower in the female chips than in the male chips. The expression of CYP1B1 declined more in the medial layer of the female chips than in the male chips. Compared with the male chips, bosentan-treated female chips showed a lower level of muscularization, determined by counting QD705+ PAH-SMCs in intimal layers. Interestingly, early treatment of bosentan decreases intimal deposition of laminin and ColT1α in the female chips than in male counterparts. As can be seen from this example, the systems and methods herein can be used to develop sex-specific therapies for a disease.

Efficacy of anti-PAH drugs in ameliorating pulmonary arterial hypertension right ventricular hypertrophy (PAH-RVH): the system can be used to identify the interactions between PAH-afflicted ECs and CMs and assessing drug efficacy.

The modified chip device can be used, for example, for growing both cardiomyocytes (CMs) in the study of cardiovascular disease, and pulmonary arterial endothelial cells (ECs) in the study of pulmonary vascular diseases. The pulmonary arterial ECs, for example, can be collected from the pulmonary arteries of healthy donors (N-ECs) and that of PAH patients (PAH-ECs). We have seen that PAH is an example of a disease that can benefit from improved treatments developed with the systems and methods taught herein. Through the growing of CMs and either N-ECs or PAH-ECs in respective compartments or channels, for example, we can measure the influence PAH-ECs on CMs by measuring various soluble cellular markers, assessing the contractility of CMs, evaluating the expression of genes by CMs, and study the influence of anti-PAH PAH drugs on the release of hypertrophy inducing agents and hypertrophic markers and CM contractility. We have seen, for example, that (i) chips prepared with CMs and N-ECs showed anisotropic growth of CMs and the presence of bundles similar to physiological CMs; and, (ii) chips prepared with CMs and PAH-ECs, CMs became hypertrophic, lost their contractility and showed elevated levels of hypertrophy related markers.

We developed a drug therapy using the systems and methods. We used two anti-PAH drugs, sildenafil and bosentan, on chips prepared with CMs and PAH-ECs, the drug reduced the extent of CM hypertrophy, improved the contractility, and reduced both hypertrophy-inducing agents and hypertrophic markers. From our study, one of skill will understand that the systems and methods can identify the interactions between PAH-afflicted ECs and CMs and assess the efficacy of anti-PAH drugs in ameliorating pulmonary arterial hypertension right ventricular hypertrophy (PAH-RVH).

Electrical Stimulation

Electricity can be applied to the cells for simulating the electrophysiological microenvironment. By modifying this device, for example, we can recapitulate the following 3 diseases: (1) venous pulmonary hypertension, (2) pulmonary embolism, and (3) chronic thromboembolic disease. In these embodiments, we can seed organ-specific cells and create microenvironment to emulate the pathological conditions of the disease. Pulmonary embolism and chronic thromboembolic disease, for example, provide a particularly important paths for uses of the systems and methods provided herein, as each is a deadly disease in which blood clots develop in the pulmonary vasculature. The systems and methods taught herein can be used to recreate pulmonary vasculature, and then to assess how blood clotting may alter the pathology of the pulmonary vascular bed by studying the interaction between the cells, and the effect of a particular treatment, such as a drug therapy, radiation therapy, or a combination thereof, for example, and how the therapy is affected by the sex of the subject, the age of the subject, some other physiological state of the subject, or a combination thereof.

It should be appreciated that vascular diseases include several pathological conditions, each of which include a pathology of arteries, veins, or lymph vessels. The systems and methods taught herein can include all common vascular diseases. For example, the systems and methods taught herein can be used to emulate, obtain data, and improve treatments of, for example, neurovascular disease, peripheral arterial disease, renal arterial disease, carotid arterial disease, aortic aneurisms, and various venous diseases that can include, for example, varicose veins, spider veins, chronic venous insufficiency, deep vein thrombosis, neurovascular disease, and lymphedema.

In some embodiments, to use the systems and methods taught herein, we will collect human cells of a relevant tissue or organ, grow the cells in the systems taught herein, and emulate the cellular interaction of each disease. As described herein, the systems are versatile and can serve many functions in the development of treatments for disease. For example, we have shown that we can determine sex-dependent differences in disease pathology, as well as screen relevant drugs for their efficacy in treating the emulated disease. It should be appreciated that the systems and methods taught herein can assist in developing precision medicine approach by studying the interaction between the cells, and the effect of a particular treatment, such as a drug therapy, radiation therapy, or a combination thereof, for example, and how the therapy is affected by the sex of the subject, the age of the subject, some other physiological state of the subject, or a combination thereof.

I claim:

1. A method of emulating a vascular disease in a subject, the method comprising:
   obtaining a system comprising:
      a microfluidic chip; and,
      a first channel adjacent to a second channel; wherein,
         the first channel contains a first aqueous cellular solution that includes a vascular endothelial cell tissue, wherein the first aqueous cellular solution is not a gel;
         the second channel contains a second aqueous cellular solution that is an aqueous cell growth media, wherein the second aqueous cellular solution is not a gel; and,
         a releasable, first aqueous interfacial film formed by the first aqueous cellular solution;
      the first channel and the second channel are connected to the chip and include
         a first port configured for injection of a first aqueous cellular solution into the first channel;
         a second port configured for injection of a second aqueous cellular solution into the second channel; and,
         a first wall with openings, the first wall shared by the first channel and the second channel, and the openings in the first wall configured to (i) form a releasable, first aqueous interfacial film across the openings of the first wall upon the injection of the first aqueous cellular solution and (ii) allow for a cellular communication to occur in the absence of a gel between the first channel and the second channel upon a release of the first interfacial film from the openings;
   injecting the first aqueous cellular solution into the first channel to introduce a first cell of the disease, the injecting forming the releasable, first aqueous interfacial film across the openings of the first wall; and,
   injecting the second aqueous cellular solution into the second channel to introduce a second cell of the disease;
   wherein,
      the first interfacial film releases after the injecting of the second aqueous solution; and,
      the first cell and the second cell communicate after the releasing of the first interfacial film to emulate the disease state.

2. The method of claim 1, wherein
   the system further includes
      a third channel;
      a third port configured for injection of a third aqueous cellular solution into the third channel, the third aqueous cellular solution including a vascular adventitial cell tissue; and,
      a second wall with openings, the second wall shared by the second channel and the third channel, and the openings in the second wall configured to (i) form a releasable, second aqueous interfacial film across the openings of the second wall upon the injection of the third aqueous cellular solution and (ii) allow for a cellular communication to occur between the second channel and the third channel upon a release of the interfacial film from the openings;
   and, the method further includes
      injecting the first aqueous cellular solution into the first channel to introduce a first cell of the disease, the injecting forming the releasable, first aqueous interfacial film across the openings of the first wall;
      injecting the third aqueous cellular solution into the third channel to introduce a third cell of the disease, the injecting forming the releasable, second aqueous interfacial film across the openings of the second wall; and,
      injecting the second aqueous cellular solution into the second channel to introduce a second cell of the disease;
   wherein,
      the first interfacial film releases after the injecting of the second aqueous solution;
      the second interfacial film releases after the injecting of the second aqueous solution;
      the first cell and the second cell communicate after the releasing of the first interfacial film to emulate the disease state; and,
      the second cell and the third cell communicate after the releasing of the second interfacial film to emulate the disease state.

3. A method of treating an emulated vascular disease with a drug, the method comprising:
   performing the method of claim 1;
   selecting a drug to treat the emulated vascular disease; and,
   administering the drug in the first channel or the second channel.

4. A method of treating an emulated vascular disease with a drug, the method comprising:
   performing the method of claim 2;
   selecting a drug to treat the emulated vascular disease; and,
   administering the drug in the first channel, the second, or the third channel.

5. A method of treating pulmonary arterial hypertension with a drug, the method comprising:
   the method of claim 2; wherein,
      the system further comprises
         a first growth medium channel having a first growth medium port and located in communication with the first channel; and,
         a second growth medium channel having a second growth medium port and located in communication with the second channel;

and, the method further comprises
    injecting the first aqueous cellular solution into the first channel to introduce a first cell of the disease to form an adventitial cell layer, the injecting forming the releasable, first aqueous interfacial film across the openings of the first wall;
    injecting the third aqueous cellular solution into the third channel to introduce a third cell of the pulmonary arterial hypertension to form an endothelial cell layer, the injecting forming the releasable, second aqueous interfacial film across the openings of the second wall; and,
    injecting the second aqueous cellular solution into the second channel to introduce a second cell of the pulmonary arterial hypertension to form a smooth muscle layer;
    selecting a drug; and,
    administering the drug to the first growth medium channel or the second growth medium channel;

wherein, the first interfacial film releases after the injecting of the second aqueous solution;

the second interfacial film releases after the injecting of the second aqueous solution;

the first cell and the second cell communicate after the releasing of the first interfacial film to emulate the pulmonary arterial hypertension; and, the second cell and the third cell communicate after the releasing of the second interfacial film to emulate the pulmonary arterial hypertension.

6. The method of claim 5, wherein the drug is selected from the group consisting of epoprostenol, riociguat, bosentan, macitentan, ambrisentan, treprostinil, sildenafil, tadalafil, selexipag, and iloprost, and combinations thereof.

7. The method of claim 5, wherein the selecting includes identifying the best drug candidate for the subject by administering each of a plurality of drugs selected from the group consisting of epoprostenol, riociguat, bosentan, macitentan, ambrisentan, treprostinil, sildenafil, tadalafil, selexipag, and iloprost, and combinations thereof, to measure the therapeutic effect, including the activity, efficacy, dose response, stability, toxicity, and/or a combination thereof, to identify the best drug candidate or formulation for the subject.

8. The method of claim 5, wherein the subject is female, and the drug is selected from the group consisting of epoprostenol, treprostinil, selexipag, ambrisentan, bosentan and macitentan.

9. The method of claim 5, wherein the subject is male, and the drug is selected from the group consisting of sildenafil and tadalafil.

10. The method of claim 1, wherein the vascular disease includes a pathology of arteries, veins, or lymph vessels.

11. The method of claim 1, wherein the vascular disease is neurovascular disease, peripheral arterial disease, renal arterial disease, carotid arterial disease, aortic aneurisms, and venous disease.

12. The method of claim 10, wherein the venous disease is selected from the group consisting of varicose veins, spider veins, chronic venous insufficiency, deep vein thrombosis, neurovascular disease, and lymphedema.

* * * * *